(12) United States Patent
Kondo et al.

(10) Patent No.: US 8,147,418 B2
(45) Date of Patent: Apr. 3, 2012

(54) BLOOD PRESSURE MEASURING CUFFS AND A BLOOD PRESSURE MEASURING DEVICE

(75) Inventors: Akira Kondo, Fujinomiya (JP); Shuichi Oonishi, Fujinomiya (JP); Masaru Nakanishi, Fujinomiya (JP); Takashi Watanabe, Fujinomiya (JP); Hitoshi Ozawa, Fujinomiya (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 651 days.

(21) Appl. No.: 12/083,060

(22) PCT Filed: Sep. 28, 2006

(86) PCT No.: PCT/JP2006/319321
§ 371 (c)(1),
(2), (4) Date: Mar. 31, 2009

(87) PCT Pub. No.: WO2007/043349
PCT Pub. Date: Apr. 19, 2007

(65) Prior Publication Data
US 2009/0264774 A1 Oct. 22, 2009

(30) Foreign Application Priority Data
Oct. 7, 2005 (JP) ................................. 2005-295486

(51) Int. Cl.
*A61B 5/02* (2006.01)
(52) U.S. Cl. ......... 600/499; 600/490; 600/485; 600/504
(58) Field of Classification Search .......... 600/481–507, 600/309, 310
See application file for complete search history.

(56) References Cited

U.S. PATENT DOCUMENTS

| 5,511,551 | A | 4/1996 | Sano et al. | |
|---|---|---|---|---|
| 5,906,582 | A * | 5/1999 | Kondo et al. | 600/500 |
| 6,575,912 | B1 * | 6/2003 | Turcott | 600/485 |
| 2002/0169381 | A1 * | 11/2002 | Asada et al. | 600/485 |
| 2003/0204148 | A1 * | 10/2003 | Lange et al. | 600/544 |

(Continued)

FOREIGN PATENT DOCUMENTS
GB 998472 7/1965
(Continued)

OTHER PUBLICATIONS
PCT/ISA/210.
PCT/ISA/237.
Official Notification of Examination issued Oct. 7, 2009 by the Taiwanese Intellectual Property Office in Taiwanese Patent Application No. 095136819, including English language translation.

(Continued)

*Primary Examiner* — Charles A Marmor, II
*Assistant Examiner* — Sunita Reddy
(74) *Attorney, Agent, or Firm* — Buchanan Ingersoll & Rooney PC

(57) ABSTRACT

The present invention enables making uniform contact with the tragus using inner and outer cuffs, each of said inner and outer cuffs being comprised of a cuff member 40 connected to a duct 4 and a cuff bladder 22 having a body 27 which is fixed onto said cuff member in an air-tight manner and can expand and contract, comprised in such manner in order to carry out accurate blood pressure measurement at any one given point in time without being affected by the pinch width of the tragus and depth to the tragus even with repeated mounting and removal from the ear auricle, and also comprised such that a lid 23 of said cuff bladder forms a pressing surface 25 in a shape of a protrusion.

7 Claims, 23 Drawing Sheets

U.S. PATENT DOCUMENTS

| | | | |
|---|---|---|---|
| 2004/0054291 A1* | 3/2004 | Schulz et al. | 600/500 |
| 2005/0041281 A1* | 2/2005 | Aoyama et al. | 359/356 |
| 2005/0049468 A1* | 3/2005 | Carlson et al. | 600/323 |
| 2005/0066975 A1* | 3/2005 | Brain | 128/207.15 |
| 2005/0141729 A1* | 6/2005 | Kanzaki et al. | 381/67 |
| 2005/0256386 A1* | 11/2005 | Chan et al. | 600/335 |
| 2006/0229488 A1* | 10/2006 | Ayre et al. | 600/17 |
| 2007/0135717 A1 | 6/2007 | Uenishi | |

FOREIGN PATENT DOCUMENTS

| | | |
|---|---|---|
| JP | 7-255687 A | 10/1995 |
| JP | 2005-6906 A | 1/2005 |
| TW | 418081 | 1/2001 |
| WO | 2005/034742 A1 | 4/2005 |

OTHER PUBLICATIONS

Tochikubo, Osamu, "Blood pressure measurement method and clinical evaluation of blood pressure," *Medical Tribune Ltd.*, 1988, pp. 58-61, Medical Tribune Group; and partial English-language translation thereof.

English-language translation of the International Preliminary Report on Patentability and accompanying Written Opinion (Forms PCT/IB/338, PCT/IB/373 and PCT/ISA/237) issued in corres. International Patent Application No. PCT/JP2006/319321, Apr. 17, 2008, The International Bureau of WIPO, Geneva, CH.

Supplementary European Search Report dated Dec. 12, 2011 issued in the corresponding European Patent Application No. 06810768.9-1526.

\* cited by examiner

F I G. 18
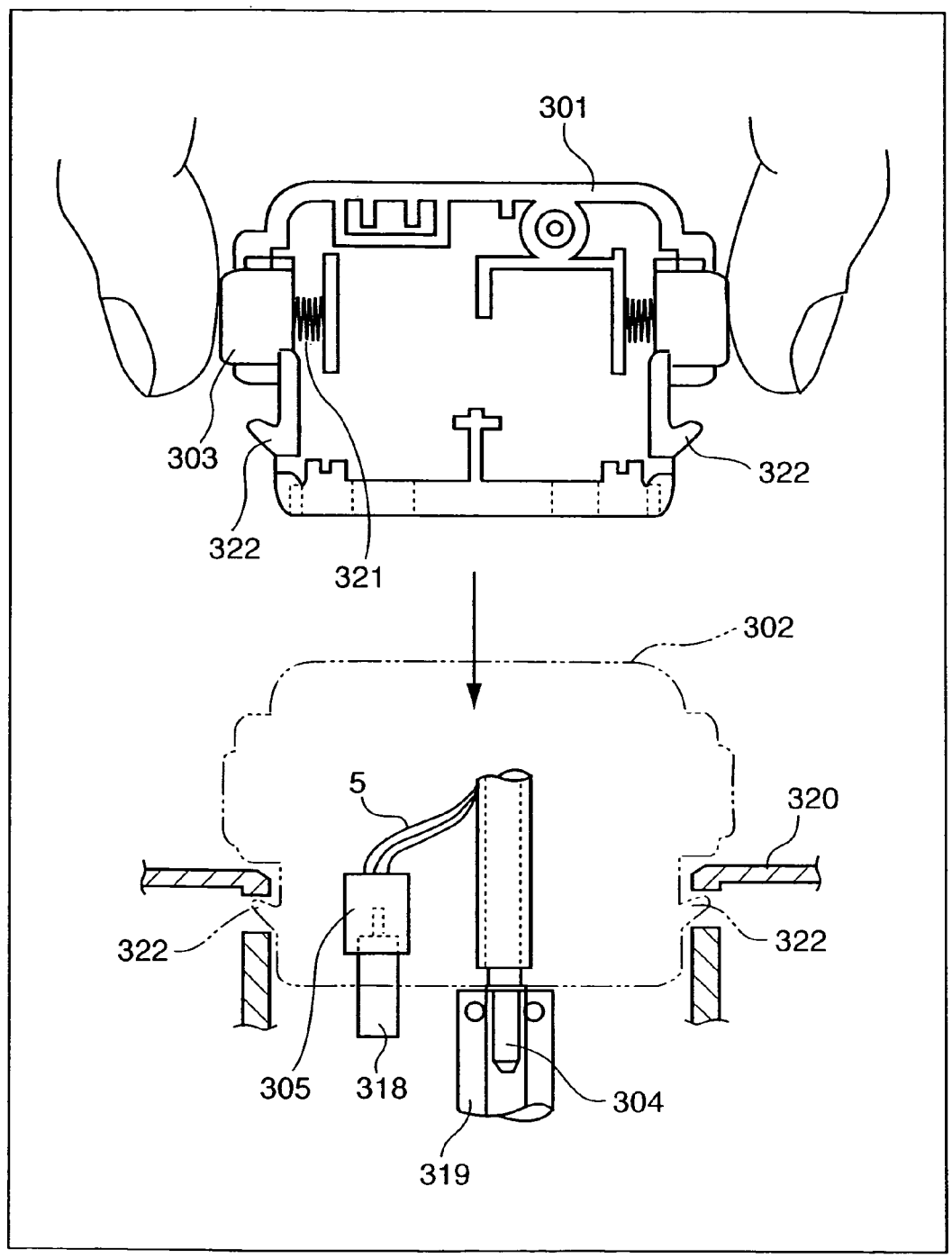

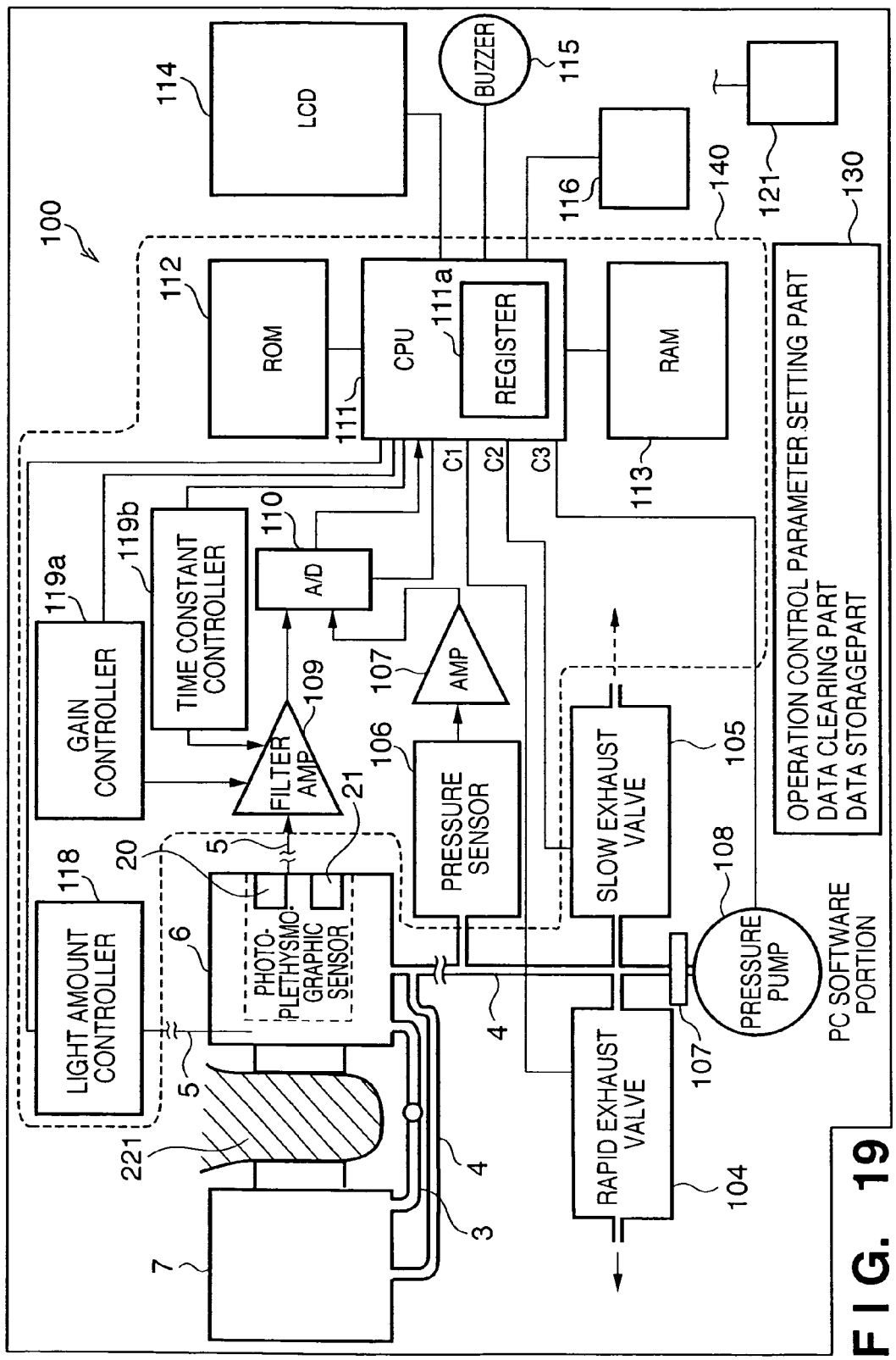
F I G. 19

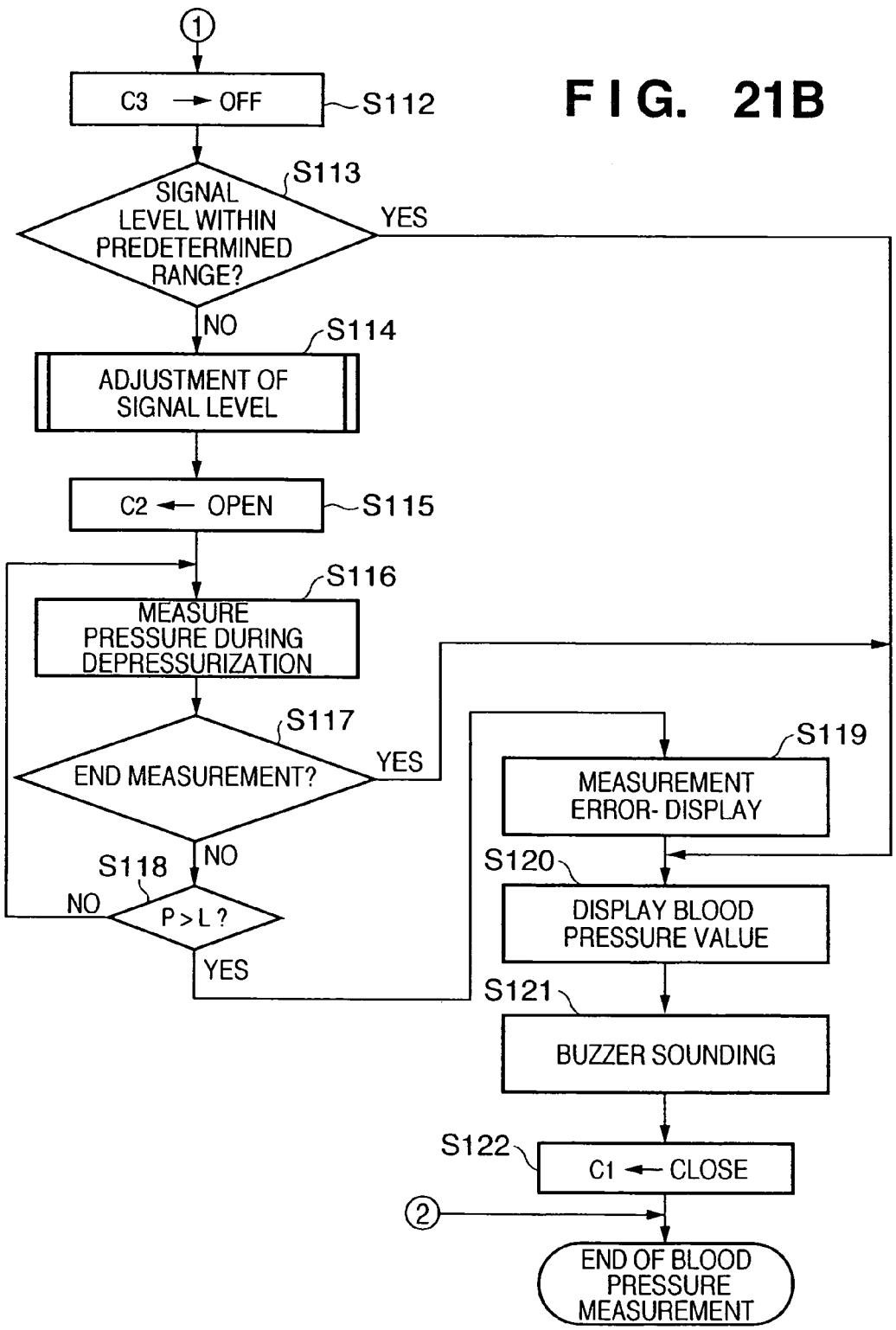

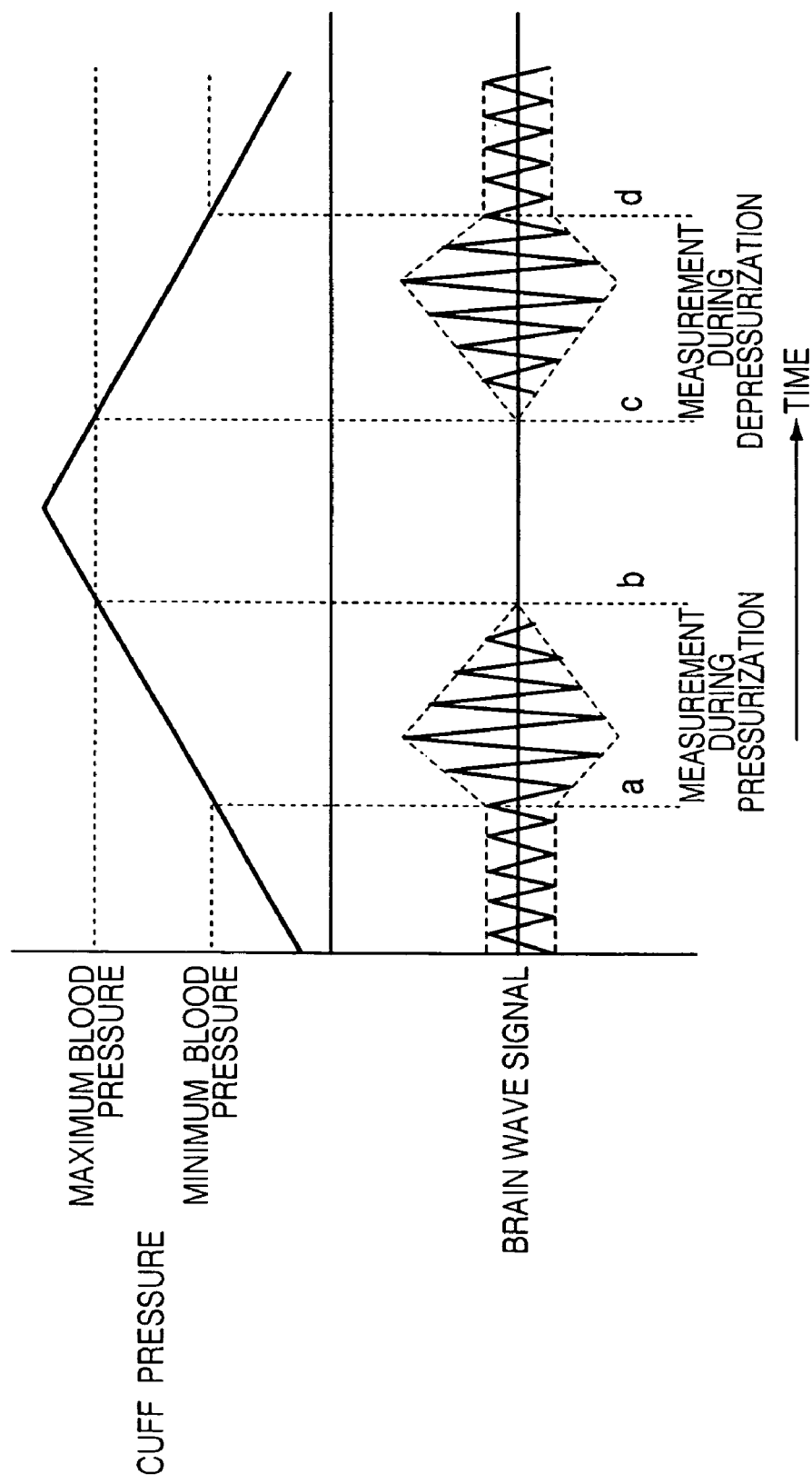

BLOOD PRESSURE MEASURING CUFFS AND A BLOOD PRESSURE MEASURING DEVICE

TECHNICAL FIELD

The present invention relates to blood pressure measuring cuffs and a blood pressure measuring device, in particular to a technique of using the external ear (auris externa) and its peripheries as portions to be measured.

BACKGROUND ART

Blood pressure changes constantly depending on changes that occur in the internal and external environments. Thus, it would be ideal to continuously record individual pulses. Even if such recording cannot be performed, it would be useful if one can continuously measure blood pressure over the course of a day, carry out such measurement on a regular basis, and monitor changes in blood pressure chronologically.

When periodically measuring blood pressure with a conventional sphygmomanometer, a cuff is wrapped around an examinee's brachium. In this case, a cuff big enough to wrap around the brachium and the main body of the sphygmomanometer comprises a blood pressure measuring device. For this, the examinee must wear the cuff on the brachium, carry the entire device with him and carry out his daily routine. However, doing so would be troublesome for the examinee. Further, the examinee will feel the discomfort of the cuff applying pressure against the brachium every time blood pressure is measured.

In order to solve such inconveniences, there is proposed a measurement method using a small cuff wrapped around the fingers. In this method, it is possible to miniaturize the entire instrument since the fingers are much smaller than the brachium (non patent reference 1). In addition, there is a method of attaching a cuff on the earlobe, applying pressure to the earlobe and thereby measuring blood pressure (patent reference 1).

According to such a method which utilizes the earlobe as the test subject, it is possible to miniaturize the blood pressure measuring instrument in comparison to those designed to be wrapped around the brachium. This also improves convenience of the device for the users.

Non patent reference 1: Osamu Tochikubo, "Blood pressure measurement method and clinical evaluation", Medical Tribune Inc. 1988, 59-61

Patent reference 1: Japanese Patent Publication Laid-Open No. 2005-6906

DISCLOSURE OF INVENTION

Problems that the Invention is to Solve

Even if blood pressure and pulse are measured at the earlobe, it is difficult to reliably and accurately measure blood pressure since blood vessels in the earlobe are extremely thin. In particular, blood vessels in the earlobe constrict when the outside temperature drops, making the measurement even harder.

Given this, by making measurements (blood pressure etc.) at the tragus that have thicker blood vessels in comparison to those in the earlobes, more reliable and accurate measurements like that measured at the brachium can be expected.

However, whereas the earlobe is soft and is exposed to the outside which makes it readily accessible, the tragus is relatively harder and its shape varies greatly from one individual to another. Thus it is not possible to utilize the cuff for the earlobe disclosed in patent document 1 for measuring blood pressure at the tragus without making modifications. In other words, even if the structure of the attachment (cuffs) of patent document 1 is employed, it would be difficult to make reliable measurements. Further, if the device is mounted on the examinee forcibly, invasiveness to the examinee will increase.

On the other hand, the tragus is known to have variances in terms of shape, size and relative position with the acoustic canal. Further, it is necessary that the inner and outer cuffs make solid contact with the tragus in order to make accurate blood pressure measurements.

Additionally, it is necessary to make sure that reliable measurements of blood pressure can always be measured without being influenced by the pinch width of the tragus and depth to the tragus even when the cuff is set to the pinch width of the tragus and fixed, and repeatedly mounted and removed.

Accordingly, the present invention is designed to address the above-mentioned problems, and has an objective of providing blood pressure measuring cuffs and blood pressure measuring device which make solid contact against the tragus with its inner and outer cuffs, and is capable of accurately making blood pressure measurements at any time without being influenced by the pinch width of the tragus and depth to the tragus even when the cuff is set to the width of the tragus and mounted and is subsequently mounted and removed repeatedly.

Means of Solving the Problems

In order to solve the above problems and achieve the goals mentioned above, the device of the present invention comprised of a blood pressure measuring cuff utilizing an inner cuff inserted into the outer ear canal and an outer cuff placed on the outside of the tragus for making blood pressure measurements, said inner and outer cuffs being comprised of a cuff member connected with a duct, and a body which can expand and shrink while at the same time is fixed to said cuff member in an air tight manner, and the lid of said cuff bladder forming a pressing surface which is either molded as a protrusion or a collapsed protrusion.

Further, said lid can be formed in a shape of either a circle, an oval or an ellipse, surface area of said pressing surface being approximately 50 to 70% and preferably about 65% of said lid, and said cuff member is formed in a shape which is congruent with the shape of said body.

Further, when said lid has a circular shape, the diameter of said cuff bladder is within a 5 to 10 mm range, the diameter of said pressing surface with in a 3 to 6 mm range, the thickness of said pressing surface is within a 0.4 to 1 mm range and preferably about 0.6 mm, and the thickness of said body is within a 0.1 to 0.8 mm and preferably about 0.25 mm.

Further, when said lid has an elliptical or an oval shape, the major axis of said cuff bladder is within a 15 to 5 mm range and preferably is about 10 mm, the minor axis is within a 10 to 4 mm range and preferably is about 8 mm, the thickness of said pressing surface is within a 0.4 to 1 mm range and preferably about 0.6 mm, and the thickness of said body is within a 0.1 to 0.8 mm and preferably about 0.25 mm.

Further, said cuff bladder is integrally molded as a single piece using an elastic material such as silicon rubber and natural rubber having a Shore hardness value of 30 to 60, preferably about 50.

Further, pulse wave detecting means is an optical means comprised of a light-emitting element (LED) and a light receiving element (phototransistor) installed inside said cuff(s) which capture signals from absorption and reflection of light caused by blood flowing through blood vessels, drilling a hole on said pressing surface after forming said cuff bladder from a light shielding material, inserting and vulcanizing an light permeable layer to said hole and integrally forming as a single piece light shielding layer, excluding the designated area of said pressing surface of said inner cuff inserted with the light permeable layer.

Further, said light permeable layer has a shape of a circle, an ellipse or an oval, and is formed concentrically or with its center off set.

Thus the present invention, which is a blood pressure measuring device, is comprised of:
  an inner cuff to be inserted into the acoustic canal,
  an outer cuff to be positioned on the outside of the tragus,
  a holding means which holds said inner cuff and outer cuff
  a pulse wave detection means which is installed inside either one of said inner cuff and outer cuff, which detects pulse wave signals from blood flowing through blood vessels,
  a pressurizing and depressurizing means, which applies or decreases pressure using a fluid body including air to said inner cuff and outer cuff that are pinching the tragus,
  ducts for supplying a fluid body connecting said inner cuff and said outer cuff to said pressure adjusting means,
  a pressure detecting means which detects pressures of said inner cuff and said outer cuff,
  a blood pressure measurement controlling method which measures blood pressure from said pulse wave signals,
  wiring which connects said pulse wave detecting means and said blood pressure measurement controlling means,
  where said inner cuff and outer cuff are comprised of said cuff member connected with said ducts and a cuff bladder having fixed onto said cuff member in an air sealed manner and a body which can expand and shrink, and forms a pressing surface shaped like a protrusion on the lid of said cuff bladder.

Effects of the Invention

According to the present invention, it is possible to make uniform contact against the tragus with the inner and outer cuffs. After fixing the pinch width of the tragus, even if the device is repeatedly mounted and removed it is still possible to reliably make blood pressure measurements without being influenced by the pinch width of the tragus and depth to the tragus.

In addition, it goes without saying that the present invention is not limited to the embodiments described below, and a variety of setups within the scope defined by the claims are possible.

DESCRIPTION OF REFERENCE NUMERALS 1 ear type sphygmomanometer
2 device main body
3 holding member
4 duct
5 wiring (signal, power supply cables)
6, 7 cuff assembly
9 covering member
10 protector
11 $1^{st}$ holding member
12 $2^{nd}$ holding member
20 light emitting element (LED)
21 light receiving element (phototransistor)
22 cuff bladder
23 lid
25 pressing surface
27 body
33 O-ring
40 cuff member

Figure 3:
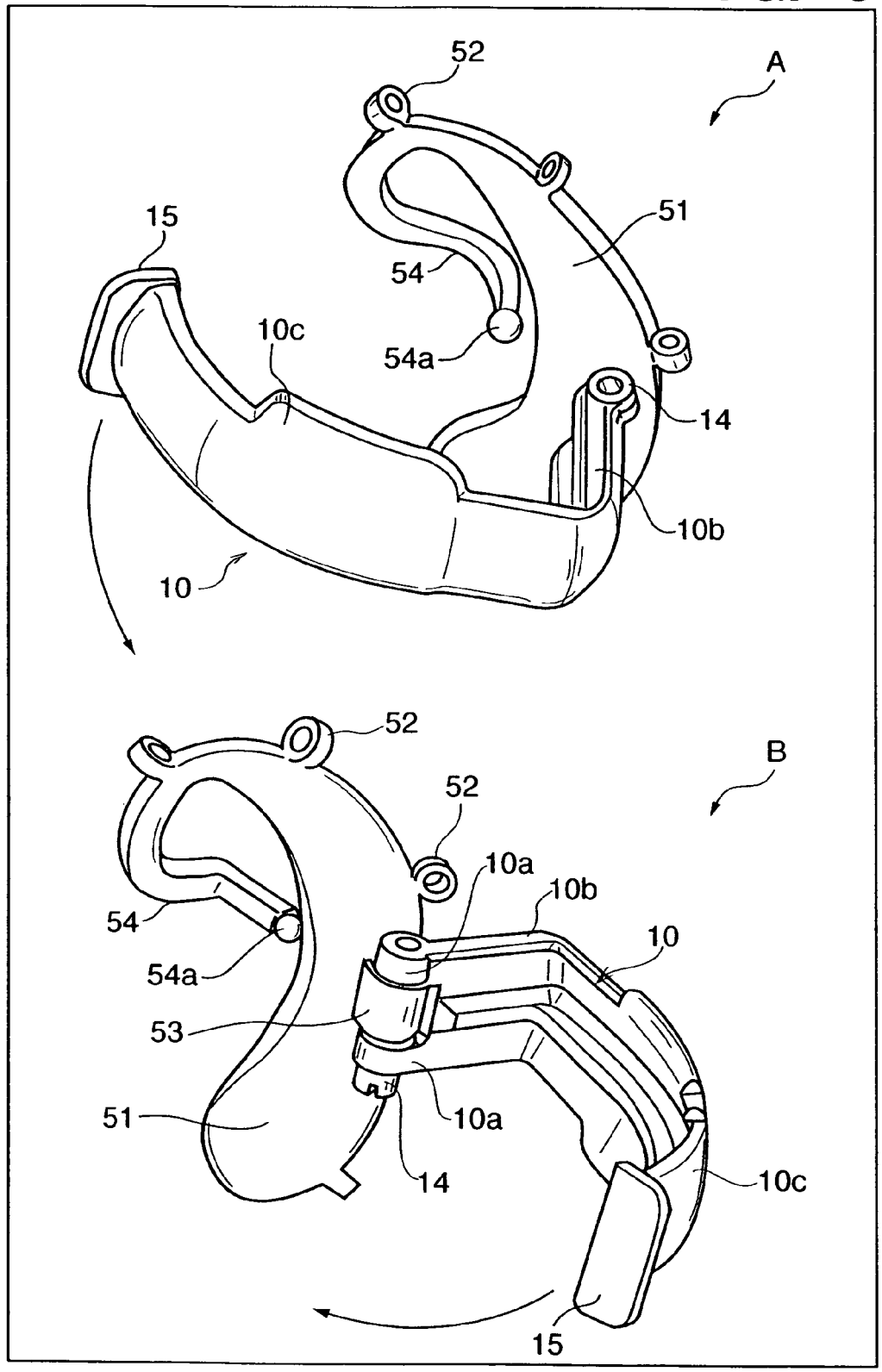

A of FIG. 3 is a perspective exterior view showing a different implementation configuration of a protector 10 which is attached to a pivot anchoring part 51, found on an edge of an ear ear-attachment member 51, via a pivot 14, shown in a usable configuration. B of FIG. 3 is a perspective exterior view of this assembly in an open state.

Figure 4:
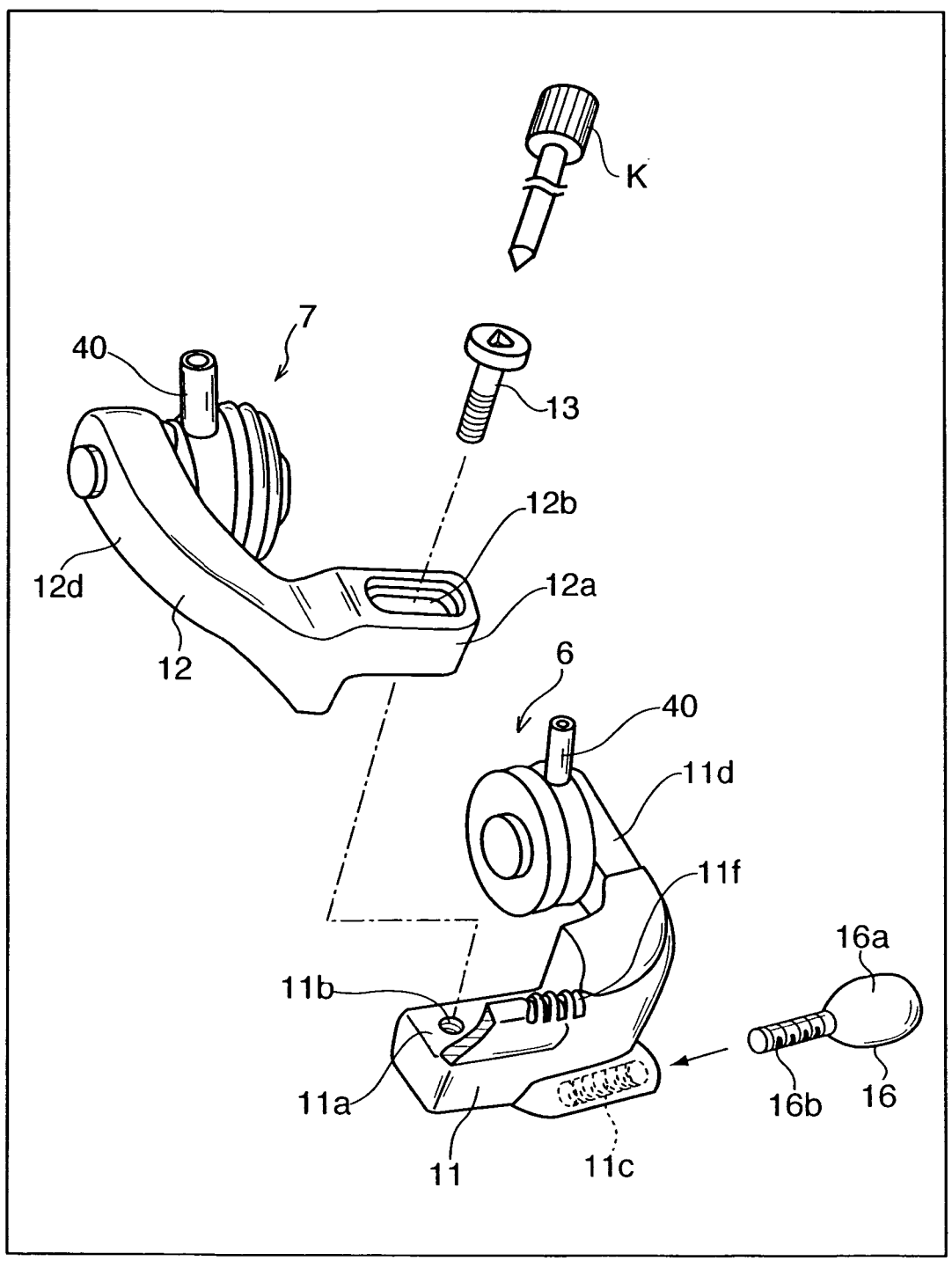

FIG. 4 is an exploded diagram of a holding member.

Figure 5:
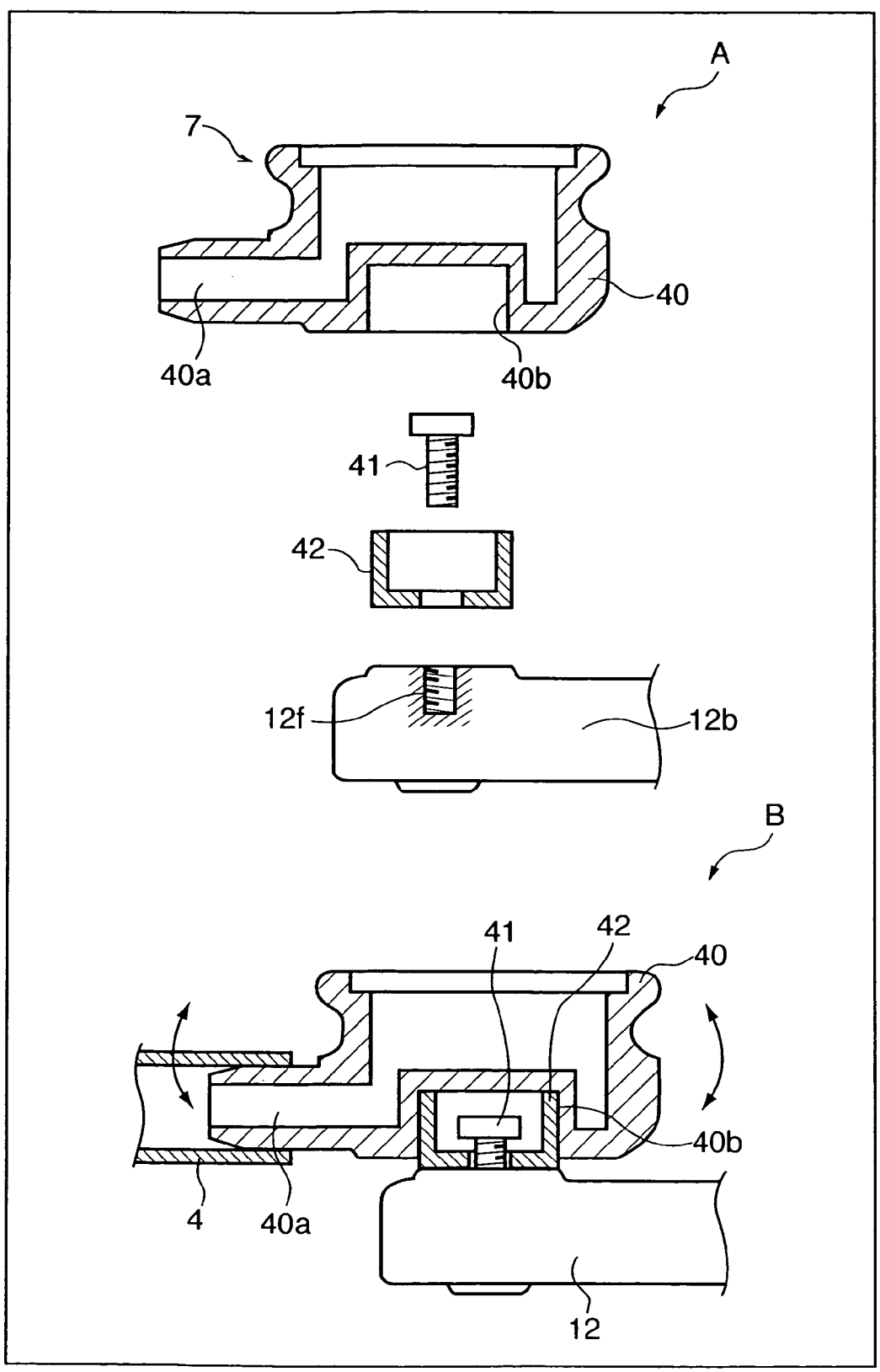

A of FIG. 5 is an exploded view of a swivel and B of FIG. 5 is a cross section of chief parts after complete assembly.

Figure 2:
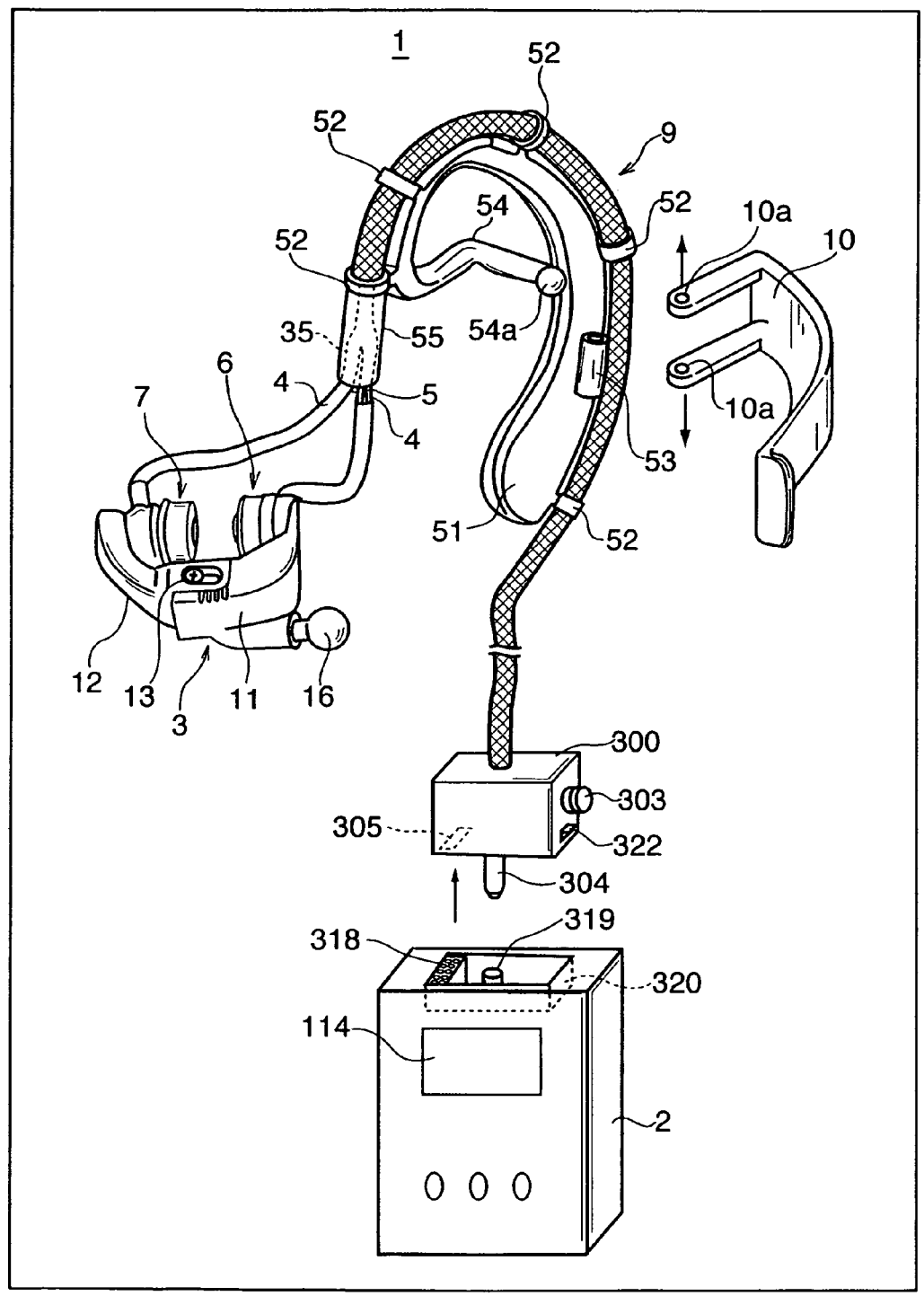
FIG. 2 is a perspective exterior view showing an example of an overall architecture of a ear-type sphygmomanometer 1.
Figure 6:
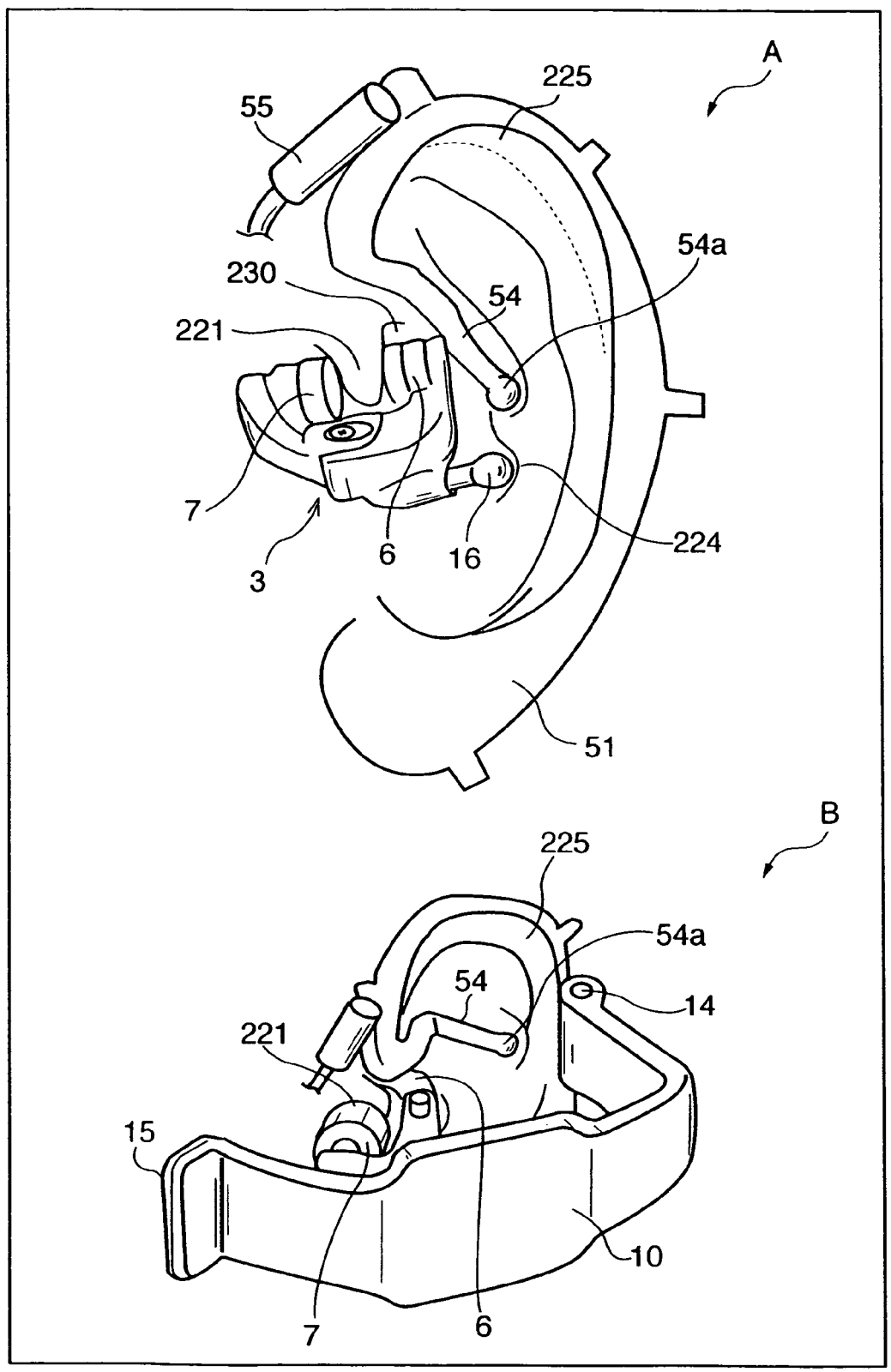

A of FIG. 6 is a perspective exterior view showing the ear-type sphygmomanometer of FIG. 2 mounted onto the ear auricle. B of FIG. 6 is a perspective exterior view illustrating usage of the protector 10.

Figure 7:
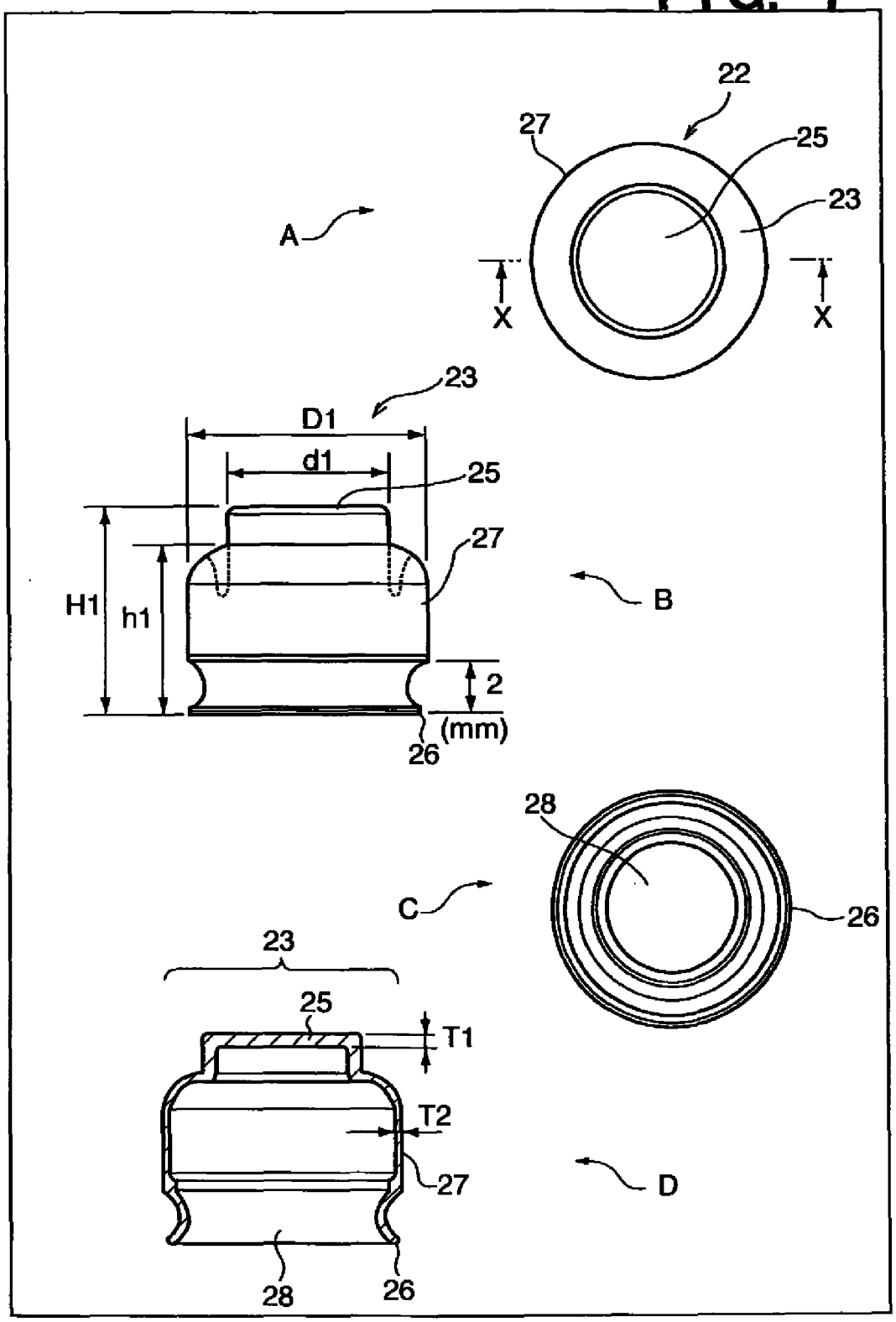

A of FIG. 7 is a plan view of a cuff bladder 22. B of FIG. 7 is a front view of the cuff bladder. C of FIG. 7 is a bottom view of the cuff bladder. D of FIG. 7 is a cross sectional view of the cuff bladder along the X-X line.

Figure 8:
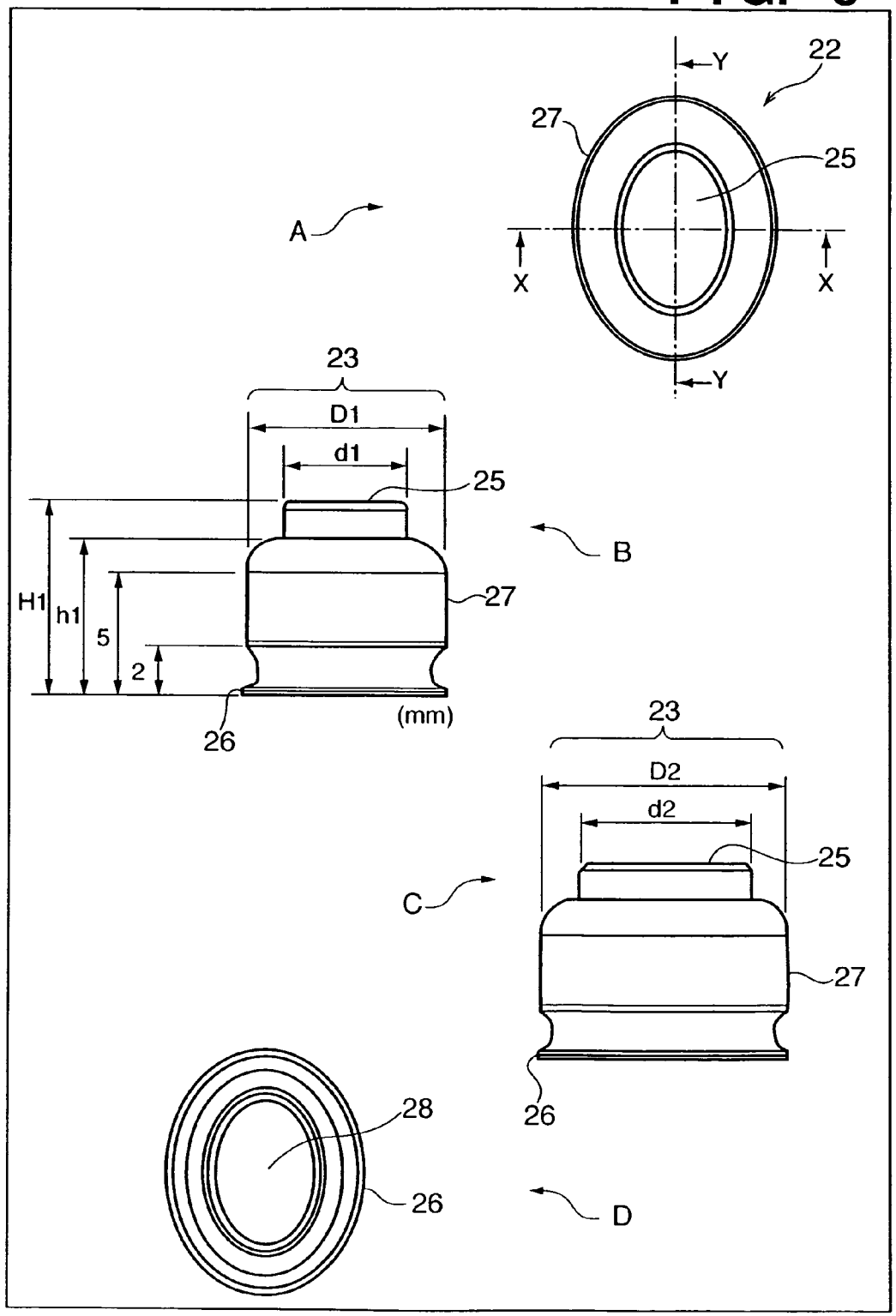

FIG. 8 shows a plan view (A), a front view (B), a left side view (C), and a bottom view (D) of the cuff bladder 22 where a lid has a shape of either an ellipse or an oval.

Figure 9:
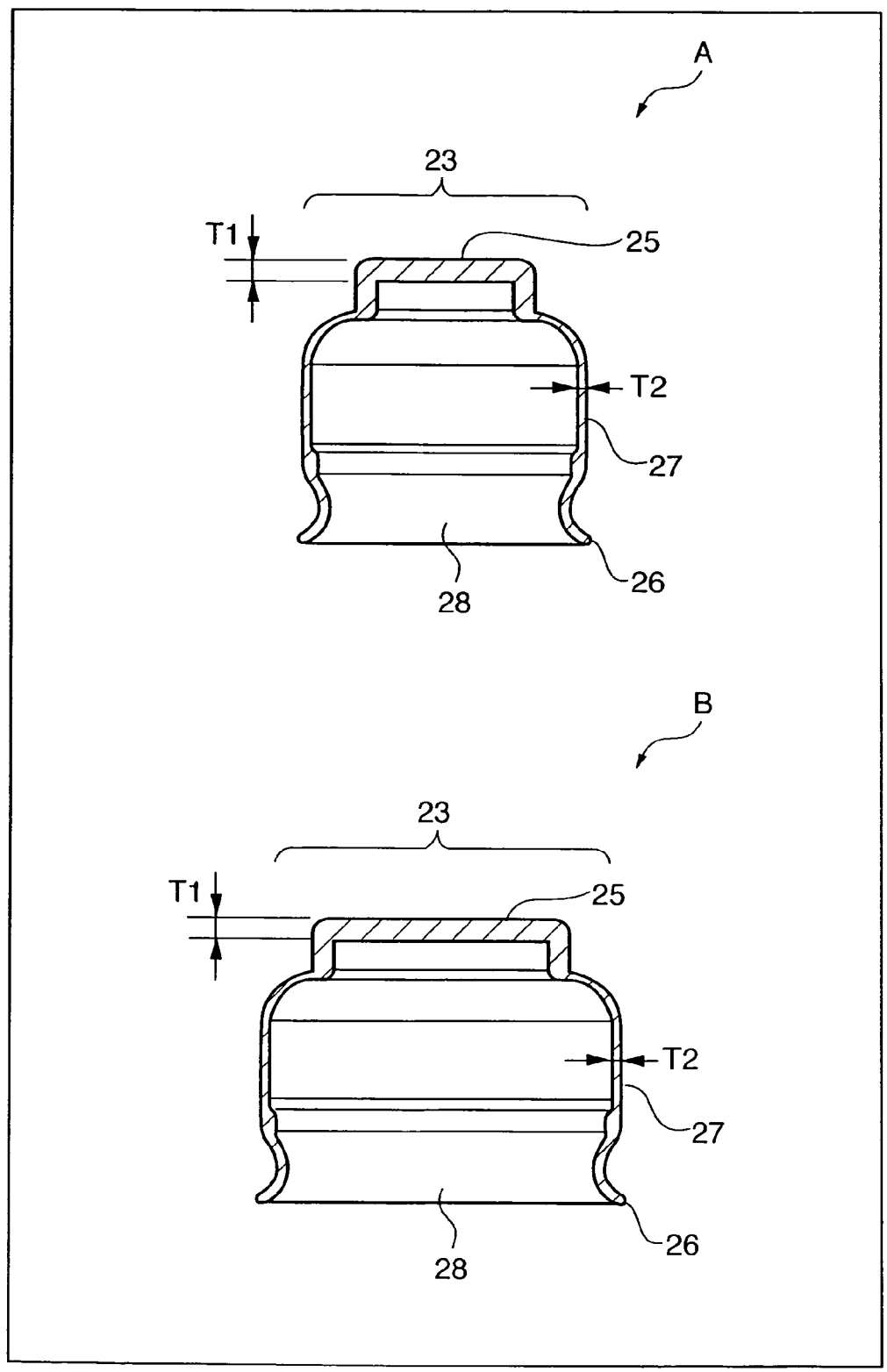

A of FIG. 9 shows a cross sectional view of FIG. 8 along the X-X line, and B of FIG. 9 shows a cross sectional view of FIG. 8 along the Y-Y line.

Figure 10:
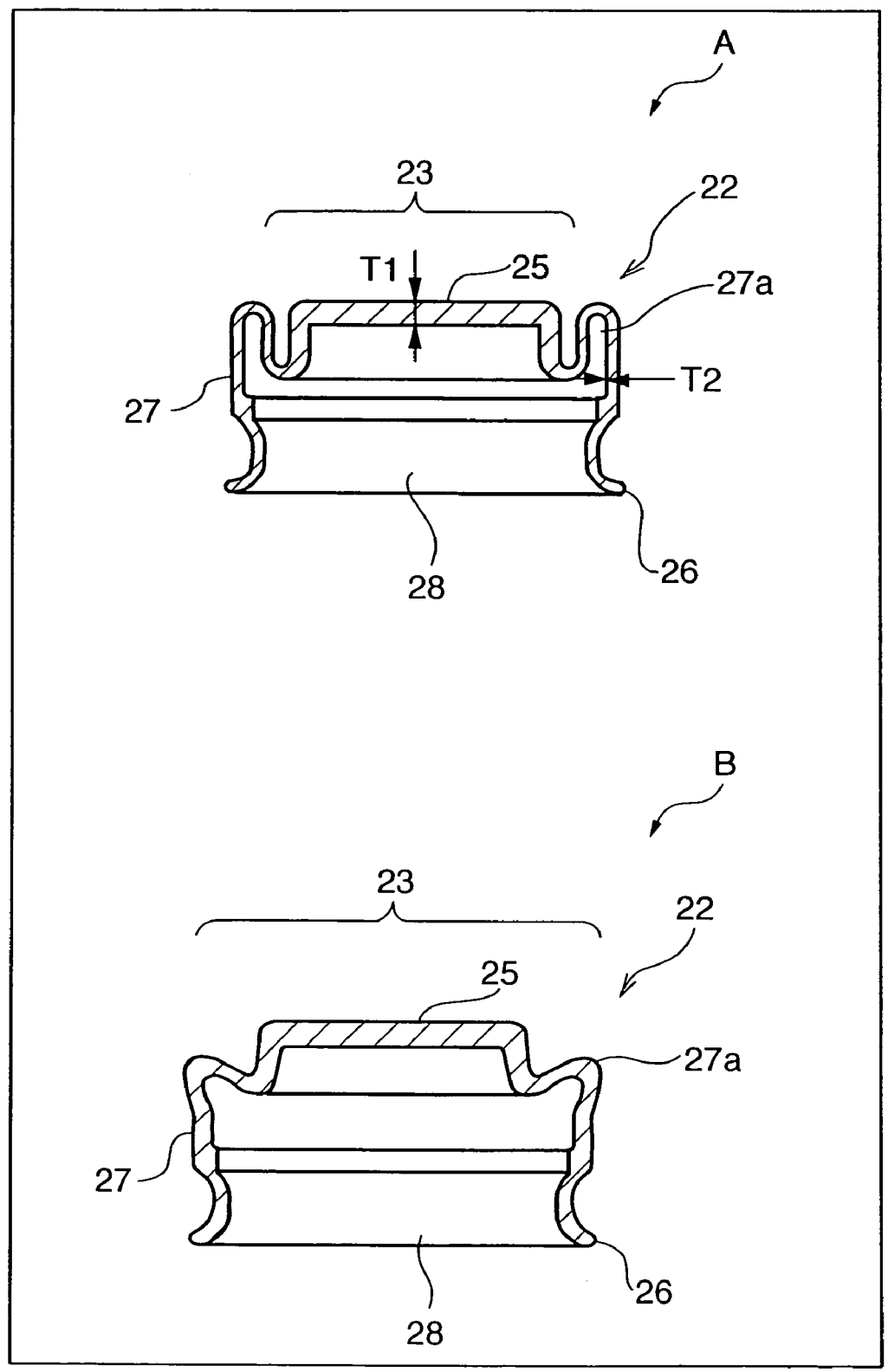

A of FIG. 10 shows a cross sectional view of the cuff bladder 22 having a pressing surface with a shape of a collapsed protrusion when pressure is withdrawn, and B of FIG. 10 shows the same when pressure is applied.

Figure 11:
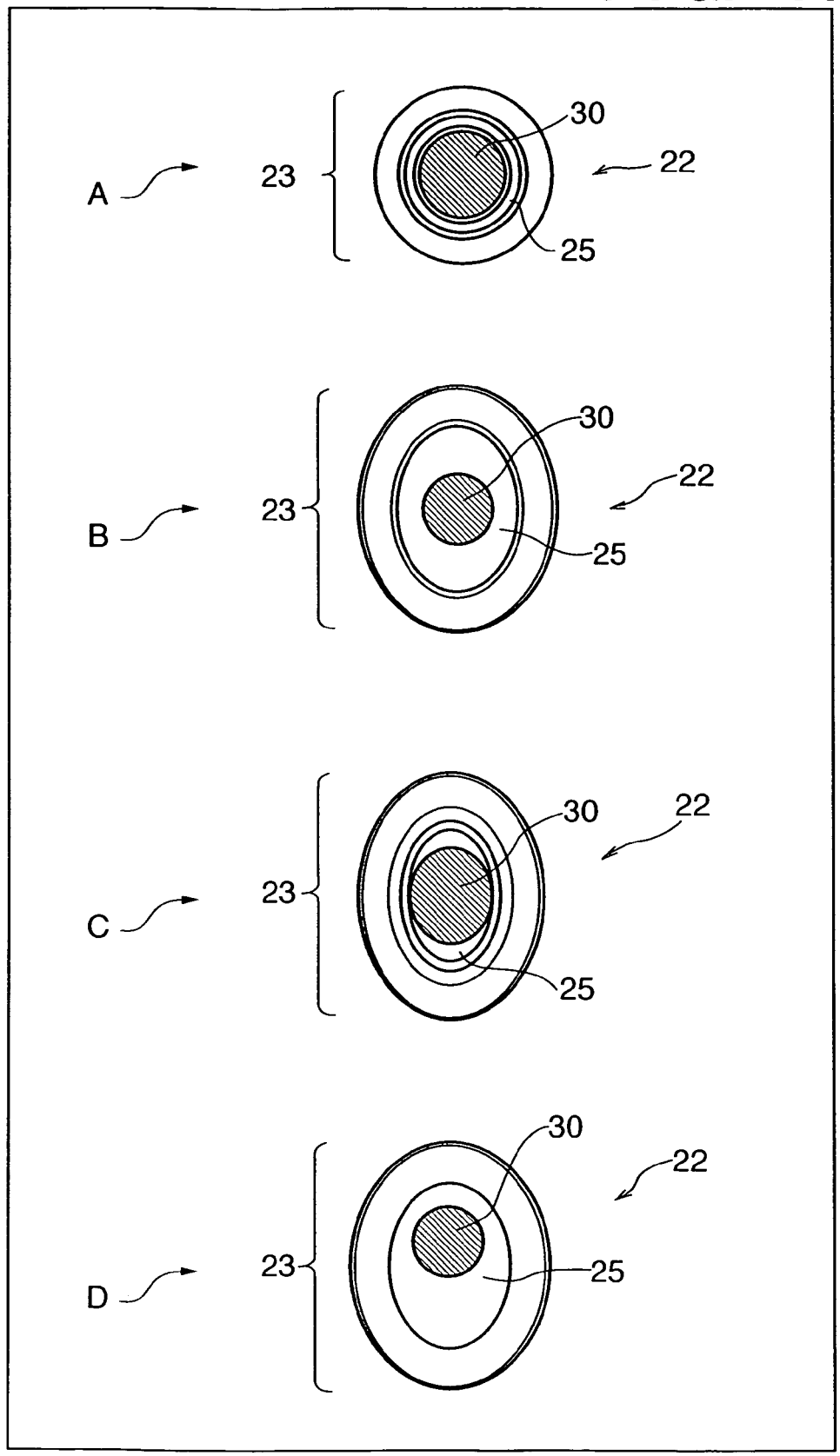

In FIG. 11, A to D are front views of the cuff bladder 22 where light shielding is applied.

Figure 12:
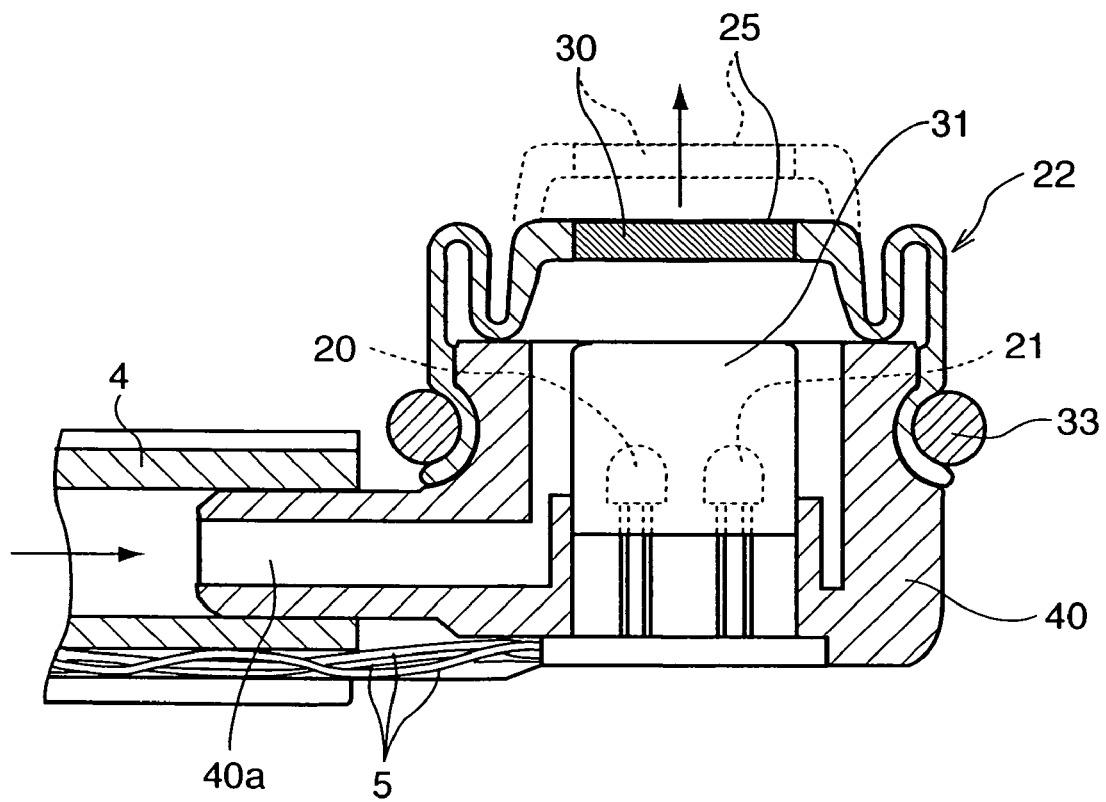

FIG. 12 is a cross section of chief parts illustrating attachment of the cuff bladder to cuff member.

Figure 13:
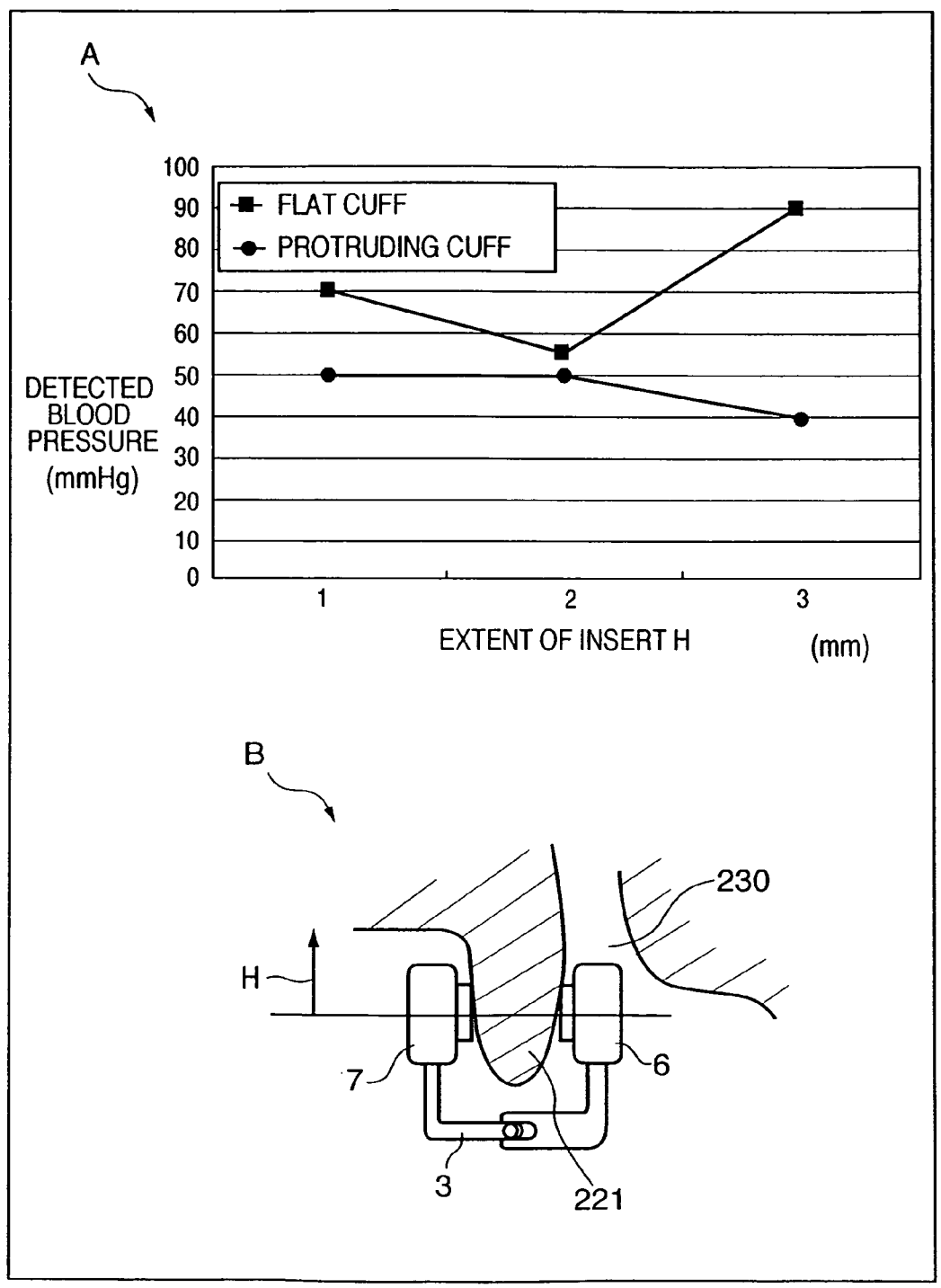

A of FIG. 13 is a graph showing the relationship between extent of insert H and detected blood pressure when two different types of cuff bladders each having either a flat lid or a protruding lid are used. B of FIG. 13 is a diagrammatic representation of the setup.

Figure 14:
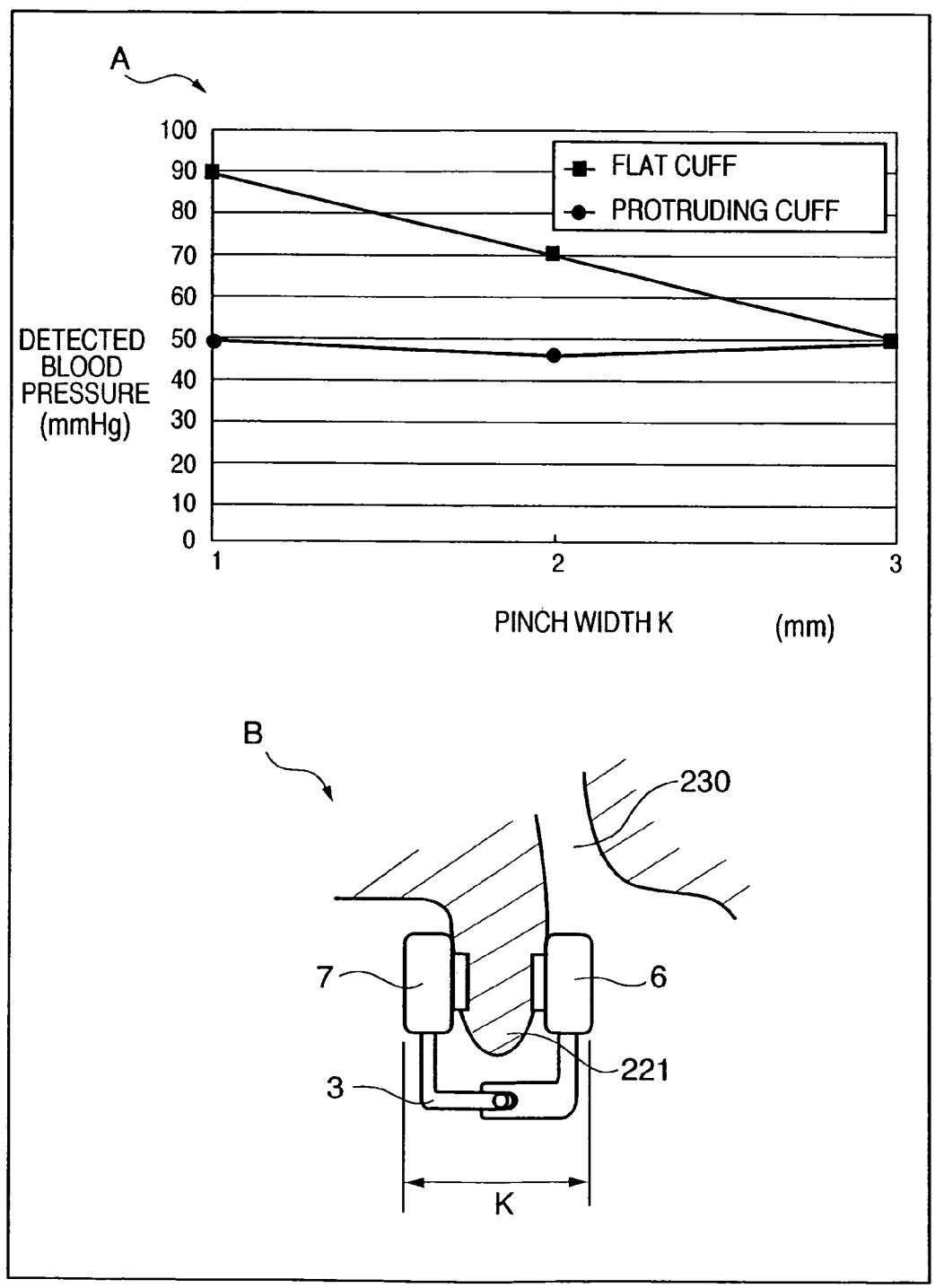

A of FIG. 14 is a graph showing the relationship between pinch width K and detected blood pressure when two different types of cuff bladders each having either a flat lid or a protruding lid are used. B of FIG. 14 is a diagrammatic representation of the setup.

Figure 15:
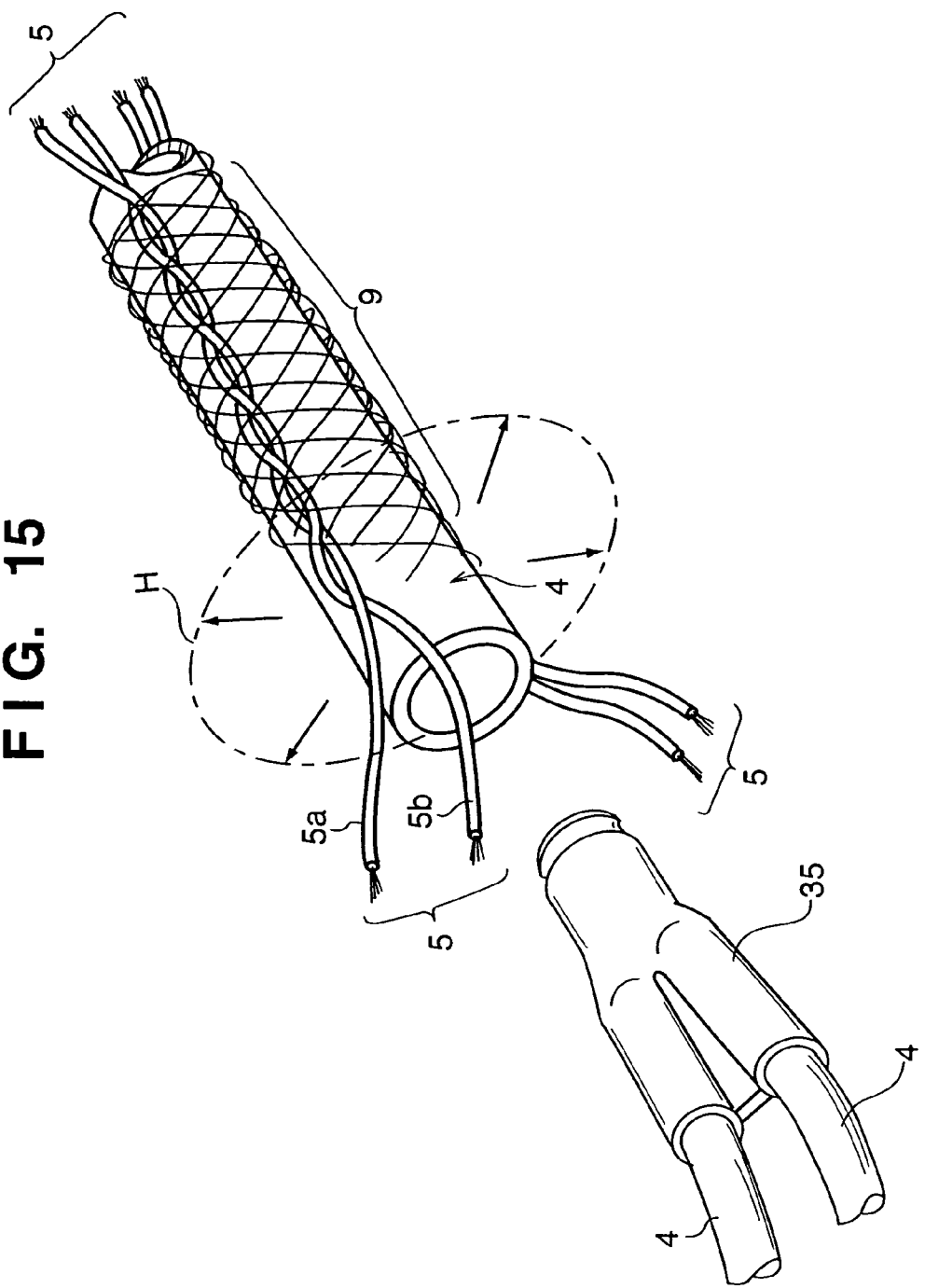

FIG. 15 is perspective exterior view of an integrated complex of wires and duct.

Figure 16:
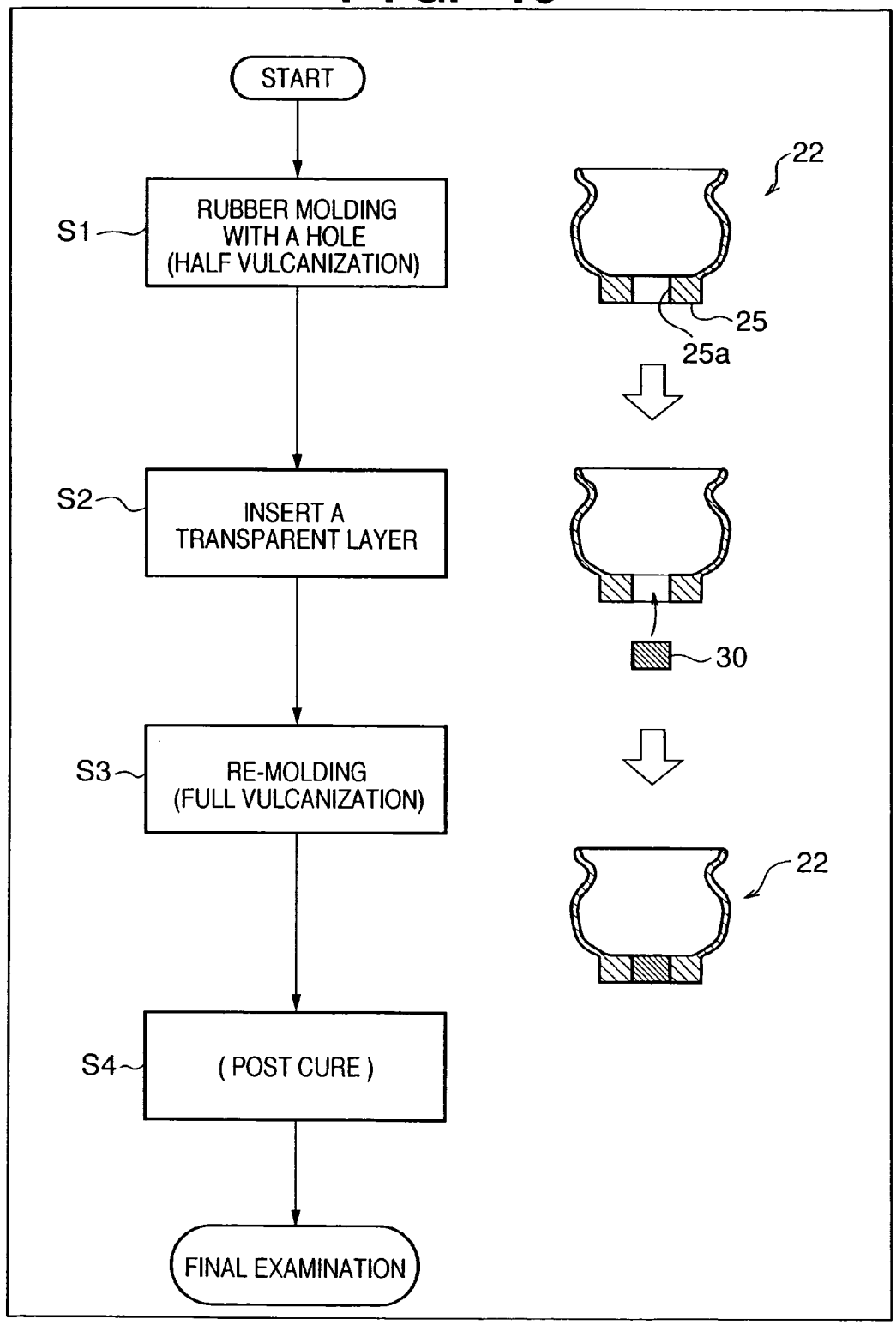

FIG. 16 is a flow chart for forming a light shielding layer inside the cuff bladder 22 and installing an light permeable layer 30, shown with cross sectional views of the cuff bladder 22.

Figure 17:
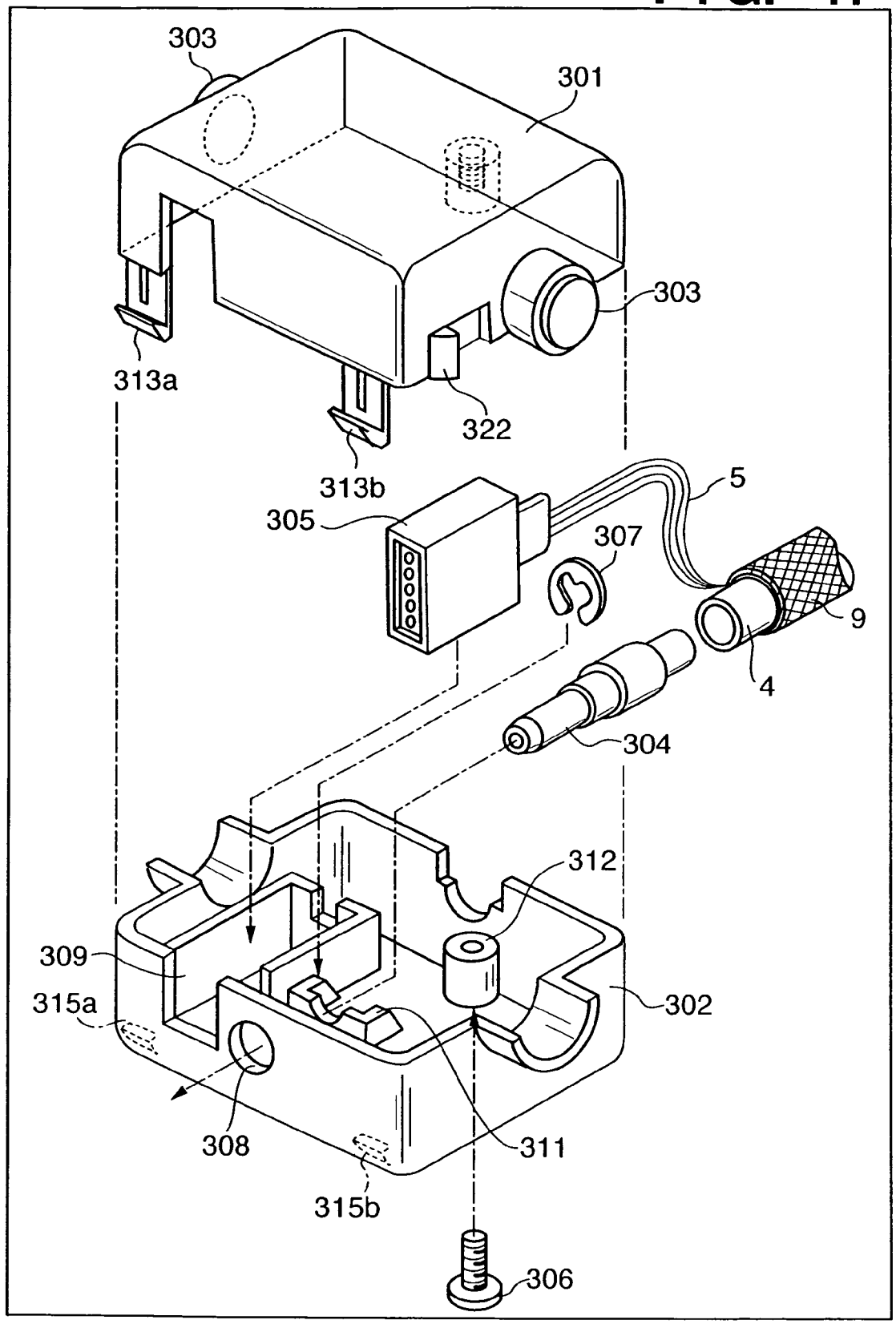

FIG. 17 is a view showing the structure of a junction 300.

FIG. 18 is a view explaining manipulation of the junction 300.

FIG. 19 is a block diagram showing the makeup of an operation circuit 100 in a device main body 2 when the ear-type sphygmomanometer 1 of FIG. 2 is structured as a photoplethysmographic sphygmomanometer.

Figure 20:
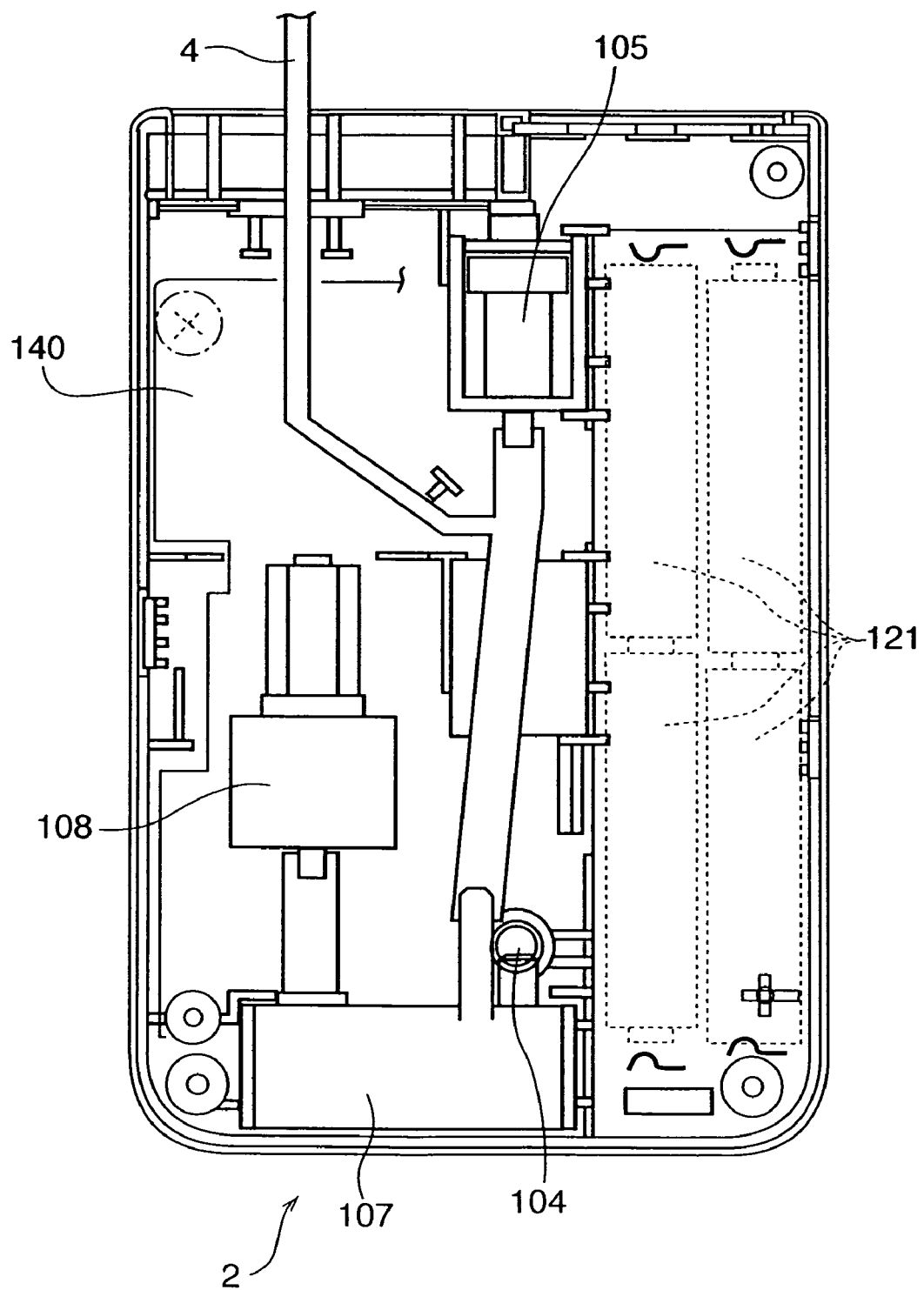

FIG. 20 is view showing an actual arrangement the device main body 2.

Figure 21A:
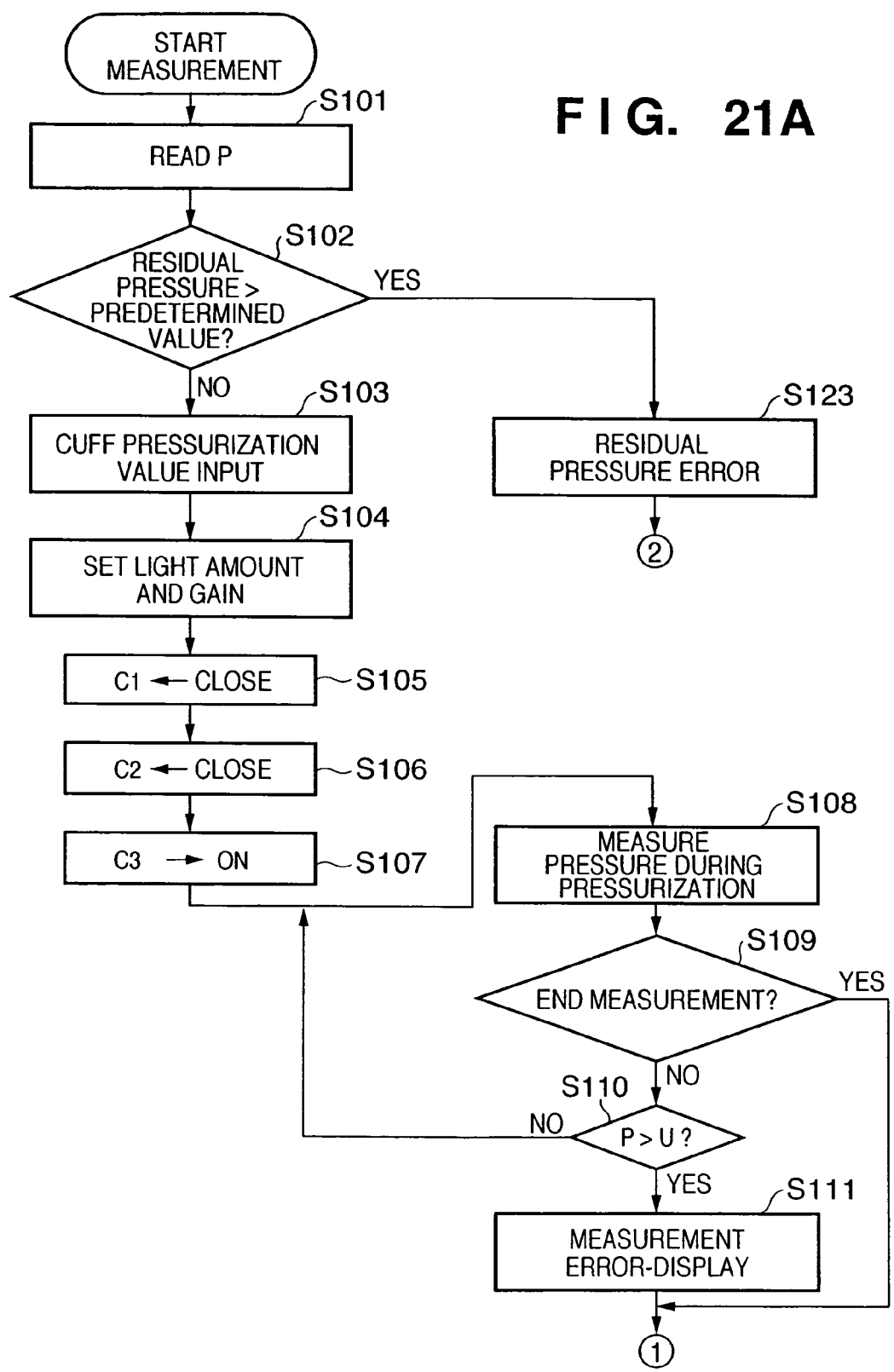

FIG. 21A is a flow chart explaining the first half of the measurement process of the ear-type sphygmomanometer (photoplethysmographic sphygmomanometer).

FIG. 21B is a flow chart explaining the second half of the measurement process of the ear-type sphygmomanometer (photoplethysmographic sphygmomanometer).

FIG. 22 is a graph showing the correlation between cuff pressure and pulse wave signal.

BEST MODE FOR CARRYING OUT THE INVENTION

First, the most unique feature of the current invention is that it uses the tragus for making blood pressure measurements. One of the reasons for selecting the tragus for making blood pressure measurements is that miniaturization of the blood pressure detecting part is possible because the tragus is a part of the auricle and is quite small in size. Further, the tragus is a part of the head which does not move as much as other body parts such as limbs and is thus well suited for measuring blood pressure. Additionally, it serves no other purpose aside from sound collection, and therefore causes little interference, compared to other body parts such as the fingers, even when attached with a cuff throughout the day. Even more, since the blood pressure detection part can be miniaturized, it is possible to reduce invasiveness which causes pain to the examinee when measuring blood pressure.

As an additional support for reducing discomfort during blood pressure measurement by utilizing the tragus, it is to be understood that body parts such as the brachium and the fingers carry out complex movements and therefore has the necessary neural network set around their blood vessels.

On the other hand, the tragus, which is a part of the auricle, is fixed on the head, and is used mostly for collecting sounds. Accordingly, the extent of neural network development around the tragus is much less than those in the brachium and the fingers that carry out complex movements. Thus, when measuring blood pressure using the outer ear and its periphery, the tragus is the place which feels the least amount of pain and discomfort, and also is small in size such that it allows miniaturization of the cuff. Hence it is possible to reduce pain and discomfort compared to making measurements at the brachium or fingers.

However, since the tragus is a small part of the auricle, it will be difficult to make accurate measurements of blood pressure unless a small blood pressure detecting part can be stably and firmly fixed onto the tragus such that it does not shift around during measurements.

The blood pressure detecting part is connected with, for example, a duct which supplies a pressurized fluid body, pressurized gas or pressurized fluid which applies pressure to the tragus, and electric wires which transmits electric power which drives the blood pressure detecting part and signals which are transmitted from the blood pressure detecting part to the device main body.

Due to this, when measuring blood pressure over a long period of time, it is not possible to make accurate measurements if, for example, the mounted position of the blood pressure detecting part is shifted by accidentally pulling the wire and duct during manipulation of the device main body.

Preferred embodiments of the present invention will be explained in detail below as examples with reference to the accompanying drawings. However, elements, shape and their seizes in the blood pressure measuring apparatus described in these embodiments are merely examples, and the scope of the present invention is not limited to these constituent elements.

Figure 1:
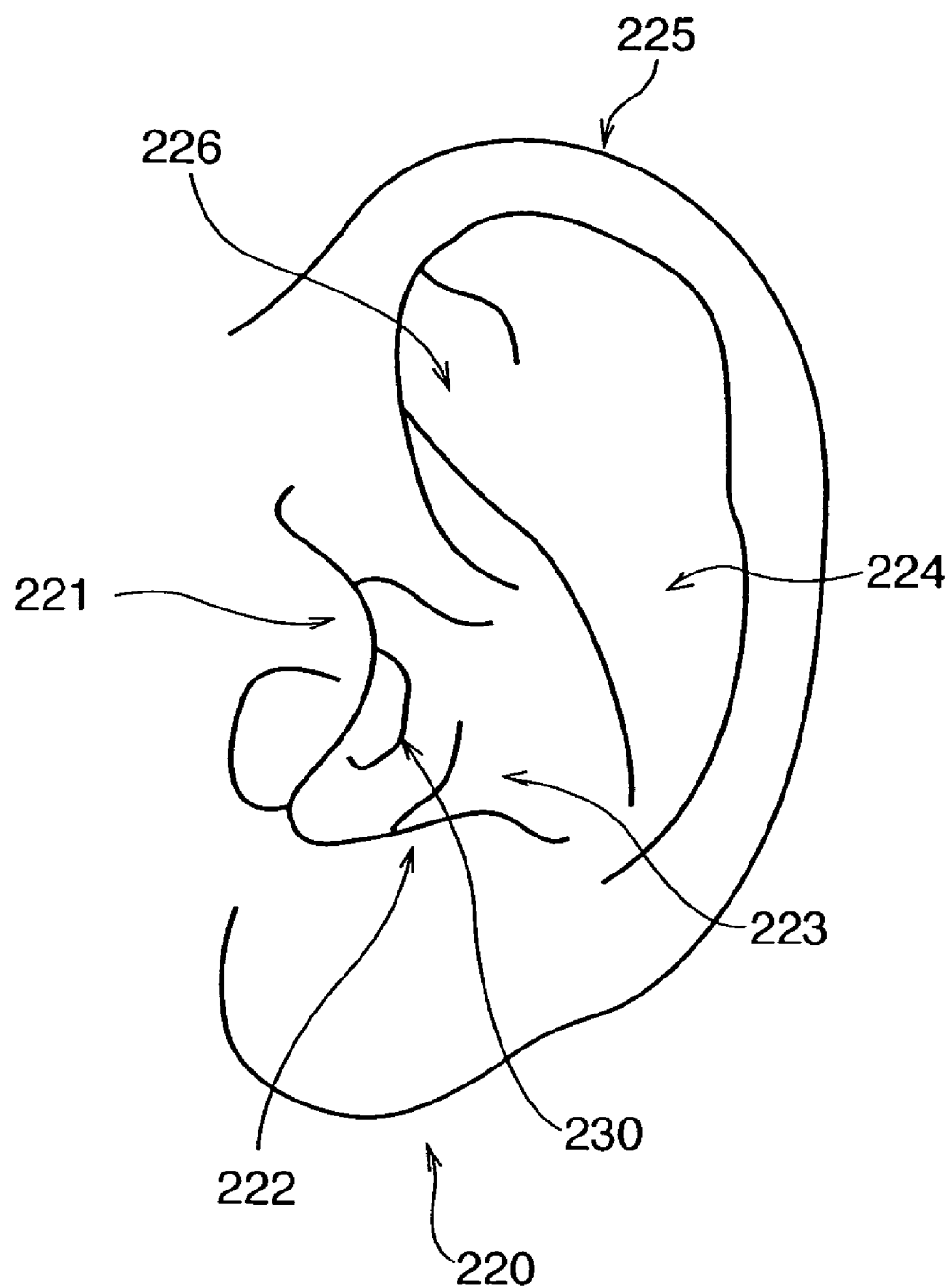
FIG. 1 is a perspective exterior view of the auricle.

First, FIG. 1 is a perspective exterior view of the left ear auricle which will be mounted with the current invention which is an ear-type sphygmomanometer 1.

In FIG. 1, an ear auricle 220, commonly referred to as an ear, has positional relations as illustrated, with tragus 221, antitragus 222, concha auriculae 223, anthelix 224, crus helicis 225 and crura antihelicis 226 which are continuously formed from the edge of acoustic duct 230. Further, on the backside of anthelix 224 is formed an extension (not shown in FIG. 1) having cartilages that are connected to the head. Sizes and shapes of each of these parts vary greatly depending on sex, age and/or race.

<Structure Of The Ear-Type Sphygmomanometer>

FIG. 2 is a perspective exterior view showing an example of the overall architecture of the ear-type sphygmomanometer 1 according to the present embodiment. In FIG. 2, the ear-type sphygmomanometer 1 has a device main body 2 for carrying out blood pressure measurement calculation, a holding member 3 which allows free attachment and detachment of cuff assemblies 6 and 7 which respectively become the inner and outer cuffs at the examinee's tragus 221, a duct 4 lined along the upper edge of an ear mounting member 51 such that the holding member 3 is suspended as shown, and the ear mounting member 51 which suspends the holding member 3 via the duct 4. In other words, the ear-type sphygmomanometer 1 is comprised of the holding member 3 which holds as shown in FIG. 2 the inner cuff assembly 6 inserted and set into the acoustic duct 230 thereby becoming the inner cuff and the outer cuff assembly 7 which is set on the outside the tragus 221 and becomes the outer cuff, and the device main body 2 connected to the holding body 3 via the duct 4 and the wiring 5.

The ear mounting member 51 is formed in a shape that allows mounting along the edge of the crus helicis 225 with the head. Further, a covering member 9 containing the duct and wiring as will be disclosed later and as shown in FIG. 2, is fixed onto the ear mounting member 51 by passing it through roughly evenly spaced loops 52 formed on the edge as integral parts of the single piece ear mounting member 51.

On the other hand, a tip 54 of the ear mounting member 51 is formed such that it curves toward the viewing position (ie.-toward the observer of FIG. 2), and forms a sphere 54a at the tip. Further, the ear mounting member 51 is shaped much like the ear mounting part of an eyeglass frame, structured such that it stabilizes the ear mounted portion of the present invention when mounted onto the crus helicis 225. The resin material to be used for forming the shape of this ear mounting member 51 as shown in FIG. 2 are polycarbonate type, ABS type, POM type and PPS type. Further, although resin materials are commonly used for their mass productivity, cost and stability in terms of shape, it is also possible to use hybrid structures made of materials including light metals, wood and paper. Further, it is acceptable to color code each of the parts for various purposes, for example, assigning orange for hospitals, blue for the general public, white for kids and so on.

The covering member 9 has, at the opposite end (opposite to the end that is connected to the holding member 3 via the duct 4 and the wiring 5), a junction 300 which is a dual connector that connects the duct 4 and the wiring 5 to the device main body 2. Further, after being passed through the last loop 52, the duct 4 is connected to a bifurcating duct (dashed line), thereby connecting to two cuffs by bifurcation into two channels, and the bifurcating duct 35 is covered with a protection cover 55.

The junction 300 is a structure which is designed to connect the duct 4 and wiring 5 covered by the covering member 9 to the device main body 2, and is designed to be detachable with a dual connectivity function. More specifically, the junction 300 is inserted into the device main body 2 until a pair of locking hooks 322 on the left and right sides of the junction 300 locks into locking holes 320. This leads to plugging in of a female connector 305 of the junction 300 to a male connector 318 of the device main body 2, and also plugging in of a duct plug 304 of the junction 300 to a duct plug hole 319 of the device main body 2. On the other hand, the junction 300 is designed such that it can be detached from the device main body 2 by pressing buttons 303, disengaging the locking hooks 322 from the locking holes 320, and pulling away from the device main body 2.

The outer cuff assembly 7 and the inner cuff assembly 6 are attached in relation to the holding member 3 in a manner which either allows free rotation or no rotation at all, such that the pressing surface evenly contacts the tragus 221 as will be stated later.

While the holding member 3 is set on the tragus 221 of the left ear by pinching, the device main body 2 can be stored in, for example, the chest pocket of the examinee or in a pouch specifically designed to store the device. If the device is to be set on the right ear, a set of the holding member 3 and the ear mounting member 51 with reversed sides (i.e. mirror image) are prepared. Further, by fixing the device using a clip when stored in the chest pocket of a shirt, it will firmly stay on the examinee and will prevent unintentional drops. Further, by arranging an LCD screen or a start switch on the top surface of the device main body, it will be possible to manipulate the device for measuring blood pressure without necessarily taking out the device out of the pocket.

<Structure of the Cuff Assemblies 6 and 7 and the Holding Member 3>

Referring to FIG. 2, the holding member 3, which is a holding means, is comprised of a $1^{st}$ holding member 11 made from a resin for holding the inner cuff assembly 6, and a second holding member 12 made of a resin for holding the outer cuff assembly 7. Each of the holding members 11 and 12 are structured, as will be discussed later, such that the inner and outer cuff assemblies 11 and 12 can be moved in parallel to each other and also can be fixed at a location after parallel movement for the purpose of adjusting the pinch width.

Further, an anthelix member 16 is built which suspends the $1^{st}$ holding member in an immobile state by making contact with the anthelix 224. This anthelix member 16 is made of a resin and has a head in the shape of a sphere as shown in FIG. 2, and forms a male screw as will be discussed later which screws into a female screw formed on the $1^{st}$ holding member 11 and allows necessary adjustments for different individuals by allowing adjustment of the amount of protrusion of the anthelix member 16.

<Structure of Protector 10>

On the side surface of the ear mounting member 51 is formed a pivot support 53, and a protector 10 made of a resin is set on this pivot support 53 in a removable, rotatable or both removable and rotatable manner. In FIG. 2, this protector 10 has a shape which covers the holding member 3 when mounted on the tragus by making contact on the temporal region of the examinee's head with the frontal portion of the protector 10, and is structured so mainly to provide protection when the examinee is rolling over during sleep. For this reason the protector 10 can be set onto the pivot support 53 via tip portions 10a which face protrusions that engages into holes drilled on top and bottom of the pivot support 53 and can be elastically deformed in directions indicated by the arrows such that it can hold the protector 10 onto the pivot support 53 during sleep.

A of FIG. 3 is a perspective exterior view showing a different implementation configuration of the protector 10 which is attached to the pivot support 53, found on an edge of the ear-attachment member 51, via a pivot 14 such that it can be used. B of FIG. 3 is a perspective exterior view of this assembly in an open state.

In FIG. 3, using the same reference numerals for parts that have already been explained, the tip of the protector 10 is covered with a cushion 15 made from sponge in order to eliminate discomfort when making contact with the temporal region of the examinee's head.

Further, an extension 10b is integrally molded as a part of the protector 10, which crosses at a right angle with a main body 10c having curvature on the outside as shown. Further, the tip portions 10a are integrally formed as parts of the extension 10 such that the extension 10 covers the pivot support 53 at the top and the bottom, and is fixed using the pivot 14 which passes through a through-hole (not shown) drilled on the pivot support 53 and screwed in thereby installing the protector 10 rotatably on the ear mounting member 51.

<Structure Of The Holding Member 3>

FIG. 4 is an exploded diagram of a holding member. In FIG. 4, using the same reference numerals for parts that have already been explained, the $1^{st}$ holding member 11 made from a resin for holding the inner cuff assembly 6 has a female screw part 11c (dashed line) which engages with a male screw 16a of the anthelix member 16 also having a spherical head 16a as shown in FIG. 4. A sliding surface 11a is formed on the first holding member 11 with walls on the front and right sides, and has a fixing screw 11b insert-molded or integrally molded. Further, an extension lid which fixes a cuff member 40 of the cuff assembly 6 is extended at a right angle. Further, teeth 11f used as increments (as a rough indication) for fine adjustment of the distance between cuffs and also for gripping, is formed as shown in FIG. 4.

On the other hand, the $2^{nd}$ holding member made from a resin is integrally molded with a sliding surface 12a which slides against the sliding surface 11a, an elongated hole 12b which passes a fixing screw 13, and an extension 12d which fixes the cuff assembly 7. By mounting this $2^{nd}$ holding member 12 against the first holding member 11 as shown in FIG. 4, they are fixed in such a manner that allows parallel movements relative to each other, and by tightening the fixing screw 13 with a specialized tool K the holding members can be fixed at a desired position adjusted by parallel sliding movement. According to the structure mentioned thus far, it is possible to flexibly adjust the pinch width of the cuff assemblies 6 and 7 against varying thicknesses of the tragus of various individuals.

<Structure Of A Swivel>

The tragus varies greatly from one individual to another in terms of its relative position to the acoustic duct, shape, size etc, and also varies greatly depending on gender, race, and age. Therefore, it is a difficult task to sustain solid contact between the inner and the outer cuffs and the tragus.

By attaching the cuffs to the holding member 3 via a swivel, it is possible to flexibly accommodate differently shaped tragi of various individuals.

A of FIG. 5 is an exploded view of a swivel and B of FIG. 5 is a cross section of chief parts after complete assembly. Using the same reference numerals for parts that have already been explained for both A and B of FIG. 5, the outer cuff assembly 7 has the cuff member 40 which forms a tube 40a which connects to the duct 4. The cuff member 40 has a plug-in hole 40b, into which a plug-in member 42 fitted with a screw 41 is inserted. The screw 41 is screwed into the screw hole of the extension 12d of the $2^{nd}$ holding member 12. After assembly, as illustrated in B of FIG. 5, the head of the screw 41 can move up, down, right, left, forward and backward, which allows the cuff assembly 7 to freely rotate.

A of FIG. 6 is a perspective exterior view showing the ear-type sphygmomanometer of FIG. 2 mounted onto the ear auricle. B of FIG. 6 is a perspective exterior view illustrating usage of the protector 10.

First, when the ear mounting member 51 is set on the crus helicis 225, the sphere 54a at the tip makes contact with the anthelix 224. Further, when the holding member with a fixed pinch width for setting the inner and outer cuffs on the tragus is set on the tragus 221 by pinching, the device is further stabilized by the anthelix member 16 making contact with the anthelix 224.

Further, the protector 10 is rotated such that the cushion 15 makes contact with the temporal region of the examinee's head.

<Structure of a Cuff Bladder>

Next, FIG. 7 is explained. A of FIG. 7 is a plan view of a cuff bladder 22. B of FIG. 7 is a front view of the cuff bladder. C of FIG. 7 is a bottom view of the cuff bladder. D of FIG. 7 is a cross sectional view of the cuff bladder along the X-X line. The cuff bladder 22 is integrally molded in a hat-like shape with a body 27 which elastically deforms when pressure is added/withdrawn and a lid 23 having a flat pressing surface 25 extended from the body and protruding and making contact with the tragus.

Further, the perimeter of an opening 28 is integrally molded as a flange 26. Further, in D of FIG. 7, by setting a $1^{st}$ measurement T1 of the pressing surface 25 to be thicker than a $2^{nd}$ measurement T2 of the body 27, the pressing surface 25 is structured to always contact the tragus with a flat surface. Further, the pressing surface 25 is designed to protrude by approximately 1.5 mm.

Further, the diameter D1 of the lid 23 is set as 5 to 10 mm in order to allow proper detection of the pulse wave, the diameter d1 of the pressing surface as 3 to 6 mm in order to secure an adequate ischemic surface area, the $1^{st}$ measurement T1 as 0.4 to 1 mm and preferably around 0.6 mm, and the $2^{nd}$ measurement T2 as 0.1 to 0.8 mm and preferably around 0.25 mm. Further, a height H1 is set as 4 to 8 mm, and h1 as 2.5 to 6.5 mm. With these setup parameters, reliable blockage of blood flow (ischemia) and appropriate detection of the pulse waves are possible, which leads to highly accurate measurements of blood pressure. Further, it is also possible to select the cuff assemblies 6 and 7 having various dimensions of cuff bladder 22 within the given parameters. Other measurements are shown in FIG. 7 in the unit of mm.

This lid 23 can be formed in a shape of a circle, an ellipse, or an oval which resembles that of a track in a sports arena, and likewise the pressing surface 25 can be formed in equivalent shapes. The cuff member is formed in a shape which fit with the cylindrical portions of these parts.

FIG. 8 shows a plan view (A), a front view (B), a left side view (C), and a bottom view (D) of the cuff 22 bladder where a lid has a shape of either an ellipse or an oval. Further, A of FIG. 9 shows a cross sectional view of FIG. 8 along the X-X line, and B of FIG. 9 shows a cross sectional view of FIG. 8 along the Y-Y line.

Using the same reference numerals for parts that have already been explained for both FIGS. 8 and 9, the major axis of the cuff bladder is within a 15 to 5 mm range and preferably is about 10 mm, the minor axis is within a 10 to 4 mm range and preferably is about 8 mm, and the surface area of the pressing surface 25 is within a 50 to 70% range of the lid 23 and preferably about 65%. Further, thickness T1 of the pressing surface is within a 0.4 to 1 mm range and preferably about 0.6 mm, and thickness T2 of the body is in a 0.1 to 0.8 mm range and preferably about 0.25 mm. These measurements are indicated in FIGS. 8 and 9 in the unit of mm.

The cuff bladder 22 is integrally molded from an elastic material including silicon rubber, natural rubber and predetermined synthetic resin materials with a Shore hardness value of 30 to 60, preferably around 50. As described, by setting the thickness T1 of the lid, having the flat pressing surface 25 extended from the body and protruding and making contact with the tragus, larger than the thickness T2 of the body, it is possible for the pressing surface 25 to maintain a flat surface when pressure is applied and the bladder expands. Further, it is also possible for the pressing surface 25 to maintain a flat surface when pressure is decreased and the bladder shrinks. Moreover, it is also possible to form the body 27 of the cuff bladder in the shape of a bellows (not shown) such that the pressing surface 25 can be moved approximately in parallel (to the baseline).

Particularly, the cuff assembly 6 which becomes the inner cuff can have a very natural insertion to the acoustic duct when shaped like an ellipse or an oval.

<The Structure of a Pressing Surface Shaped as a Collapsed Protrusion>

A of FIG. 10 shows a cross sectional view of the cuff bladder 22 having a pressing surface with a shape of a collapsed protrusion when pressure is decreased, and B of FIG. 10 shows the same when pressure is applied.

Using the same reference numerals for parts that have already been explained for FIG. 10, although the pressing surface can be formed as a protrusion as previously discussed, this could cause discomfort when mounted onto the ear auricle.

In order to address this, by forming a cuff bladder in which the pressing surface is aligned (i.e. on the same surface) with a perimeter 27a of the body 27 when pressure is decreased, and protrude above the perimeter 27a when pressure is applied, it is possible to attain a comfortable fit.

In order to make faster and more accurate measurements of blood pressure using the ear-type sphygmomanometer 1 utilizing the tragus as the subject of blood pressure measurement, it is necessary to supply pressurizing air to each of the cuffs with a pressurizing pump driven by batteries. However, battery consumption by such pressurizing pump will be rather quick and long term measurements cannot be made. In such a case, it is possible to employ a hand-driven pump. Further, as a pressurized fluid medium, various fluids can be used, such as air when using a gas, or water, oils including silicon oil and alcohol when using a liquid.

<The Structure of an Light Permeable Layer 30>

If a light emitting element (LED) 20 and a phototransistor 21 which optically detect pulse waves are installed inside the cuff, a portion of the cuff will be exposed to the outside when the inner and outer cuffs are mounted on the tragus. Therefore, measurements might be adversely affected by disturbance light, especially when the examinee goes outside and is exposed to direct sunlight including ultraviolet light.

A to D in FIG. 11 are front views of the cuff bladder 22 where light shielding is applied. Using the same reference numerals for parts that have already been explained for FIG. 11, the cuff bladder 22 is integrally molded from a transparent or light transmitting elastic material including silicon rubber, natural rubber and predetermined synthetic resin materials with a Shore hardness value of 30 to 60, preferably around 50. In addition, the cuff bladder 22 is set against the cuff member 40 (see FIG. 12) in an air-tight manner, and elastically deforms between pressurized and depressurized condition, with the pressing surface 30 moving approximately in parallel.

With this setup, the cuff bladder 22 is either transparent, half-transparent, or light transmitting, and this allows disturbance light to penetrate into the cuff bladder. Because of this, accurate measurements of blood pressure are not possible because the highly sensitive sensors are affected by the sunlight.

In order to address this, by forming the cuff bladder 22 from a material that does not transmit light and forming a light permeable layer 30 on the pressing surface 25, it is possible to block disturbance light from entering the cuff bladder, and accurate measurements of blood pressure can be made by irradiating light only on the subject for blood pressure measurement and detecting reflection. This light permeable layer 30 is formed in a shape of a circle with a diameter of 3 mm if the pressing surface 25 is circular. Further, if the pressing surface 25 is elliptical, the light permeable layer 30 is shaped as an ellipse with a major axis of 3.4 mm and a minor axis of 2.9 mm. Further, it can be off set to one side as shown D of FIG. 11 in order to make it closer to the temporal head of the tragus.

<The Structure Of The Cuff Assembly>

FIG. 12 is a cross section of the cuff assembly utilizing the cuff bladder 22 of FIG. 10. Using the same reference numerals for parts that have already been explained for FIG. 12, the inner cuff assembly 6 which is to be set on the acoustic canal located on the inside of the tragus, has the LED 20 and the phototransistor 21 built in, and also has a cuff bladder 22 fixed with an O-ring 33 on the cuff member 40 having the tube 40a which connects with the duct 4.

Further, the outer cuff assembly 7 which is to be set on the outside of the tragus, has the cuff bladder 22 fixed with an identical O-ring 33 on the cuff member connected to the bifurcated duct 4. Each of these cuff bladders 22 is basically of the same shape, and it is possible to have a shape of either a circle, an ellipse or an oval. The cuff bladder 22 can be made from materials such as silicon rubber and is fixed air-tight as shown in FIG. 12 with the O-ring 33.

According to the structure explained above, the body 27 expands when air pressure is applied from a pressurizing pump 108 via a condenser tank 107, and shrinks when pressure is decreased. It is designed to repeat these movements.

In order to carry out accurate measurements of blood pressure using the tragus as the subject, our attention was drawn to making uniform contact with a flat surfaced inner and outer cuffs against the inner and outer surfaces of the tragus, and the inner and outer cuffs being held facing each other, in addition to applying and decreasing pressure to the tragus as stated above. The inner and outer cuffs being held facing each other is achieved using the swivel which can be adjusted three-dimensionally as described above, but it was rather difficult to make uniform contact against the inner and outer surfaces of the tragus with the inner and outer cuffs kept in a flat state. In order to address this, after a long process of trial and error, we found out that having the pressing surface 25 as a protrusion as discussed above leads to the best result.

<The Effect of a Protruding Pressing Surface 25>

A of FIG. 13 is a graph showing the relationship between extent of insert H and detected blood pressure when two different types of cuff bladders each having either a flat lid or a protruding lid are used. B of FIG. 13 is a diagrammatic representation of the setup.

As can be understood from FIG. 13, with a cuff bladder having a protruding pressing surface 25, blood pressure of 50 mm Hg is detected when the extent of insert H is 1 to 2 mm, and the detected blood pressure decreases slightly and stabilizes when the extent of insert is increased to 3 mm. On the other hand, when a flat lid was used, the detected blood pressure varied greatly. Accordingly, with the use of a cuff bladder having a protruding pressing surface, it is possible to make accurate measurements of blood pressure without being affected by the extent of insert, especially when the device is repeatedly worn and removed.

Further, A of FIG. 14 is a graph showing the relationship between pinch width K and detected blood pressure when two different types of cuff bladders each having either a flat lid or a protruding lid are used. B of FIG. 14 is a diagrammatic representation of the setup.

As can be understood from FIG. 14, when a cuff bladder 22 having a protruding pressing surface 25 is used, 50 mmHg of blood pressure was detected in a pinch width range of 1 to 3 mm. In contrast, with a cuff bladder 22 having a cuff with a flat lid, the detected blood pressure decreases when the pinch width K is increased from 1 to 3 mm. Accordingly, with the use of a cuff bladder having a protruding pressing surface, it is possible to make accurate measurements of blood pressure without being affected by the pinch width, especially when the device is repeatedly worn and removed.

<Integral Structure of the Duct 4 and Wiring 5>

In FIG. 2, the duct 4 and the wiring 5 are covered with a covering member 9 so as to prevent tangling with each other. On the other hand, the duct 4 forms a centrum along the length of the duct which acts as a channel for the flow of fluid bodies including air, and it is possible to pass the wiring 5 through this centrum in order to prevent the wiring from being exposed to the outside. However, such structuring would necessitate use of a seal in order to ensure air-tightness at places where the wiring 5 exits from the duct 4. The duct 4 is a flexible structure which can be freely bent, and this makes it difficult to ensure the air-tightness and long term durability. Further, it makes the assembly work difficult as well. In order to address this issue, several arrangements of integral duct and wiring, which can improve air-tightness and assembly work efficiency, were examined.

As a result of the examination, the arrangement illustrated in FIG. 15 was shown to be the most effective, where wirings 5, 5 are laid down on the outside of the duct 4 along the length, and the wirings 5, 5 and duct 4 are covered with an elastic covering member 9 thereby integrating into a single structure.

To be more precise, the wiring 5 connected to said light emitting member and light receiving member are twisted wiring 5a and 5b, the duct 4 is formed from an elastic material including silicon rubber, natural rubber and a predetermined synthetic resin, with a centrum that makes it an air duct, and the covering member 9 is formed like a mesh from a fiber such as nylon having a predetermined thread size. Further, in order to improve noise resistance, the covering member 9 can be treated, according to need, with a metal coating film and provide an additional layer (not shown).

When integrating the duct 4 and the wiring 5 as shown above, for example, if one end is fixed in the setup shown in FIG. 15, it is possible to freely bend the integrated duct and wiring within the range shown by the dashed line in directions shown by arrows. Further, it is possible to directly pull out wiring 5 from the outer surface of the duct 4 (the wiring 5 are on the outside surface of the duct 4), which makes sealing unnecessary. Further, if metal coating is applied on top of the covering member 9, it is possible to improve noise resistance. Further, the bifurcating duct 35 can be miniaturized as shown in FIG. 15, which then can fit nicely on the tip of the ear mounting member 51.

<Cuff Bladder with a Light Shielding Layer>

FIG. 16 is a flow chart for forming a light shielding layer inside cuff bladder 22 and installing an light permeable layer 30, shown with cross sectional views of cuff bladder 22.

According to FIG. 16, an opening 25a is integrally molded on the pressing surface 25 as shown in FIG. 16 from a silicon-type material mixed with a colorant including carbon black by a rubber molding device in step S1. At this time, the ingredient is semi-vulcanized. Then, quality selection is carried out. Next, in step S2, the light permeable layer 30 formed from a transparent silicon-type material is inserted into the opening 25a. Then, when re-molding in step S3, it is set in a given mold and is integrated into a single piece by full vulcanization.

Subsequently, post-crosslinking of step S4 is carried out according to need and appearance check is performed in order to see if there are any contaminants or undesirable protrusions at the opening and select non-defective units. The cuff bladders 22 formed according to above mentioned production processes are attached as illustrated in FIG. 12 and used.

Also, the light shielding layer can be formed on either the inner or outer surfaces of the cuff bladder 22.

<The Structure of the Junction 300>

FIG. 17 is a view showing the structure of the junction 300. In FIG. 17, the junction 300 is comprised of an upper lid member 301 and a storage member 302. The duct 4 and wiring 5 are stored in the storage member 302. A duct plug 304 is attached to the end of the duct 4, and a female connector 305 is attached to the end of wiring 5. The female connector 305 is inserted into a connector storage 309. Further, the duct plug 304 is placed on a plug installation 311, and is fixed at this location with an E-ring 307. When the duct plug 304 is installed in place, a certain length of its tip projects out of a projection hole 308.

With the duct plug 304 and the female connector 305 installed in their respective places, the upper lid member 301 is attached from the top. Then, upper lid locking hooks 313a and 313b locks into storage locking holes 315a and 315b. In this state, the upper lid 301 and the storage member 302 are fixed by tightening a screw 306.

FIG. 18 is a view showing attachment of the junction 300 to the device main body 2. In order to make the attachment mechanism easier to understand, only portions of the upper lid 301 are illustrated prior to attachment, and only portions of the storage member 302 are illustrated after attachment.

As shown in FIG. 17, buttons 303 are attached to the upper lid 301 via springs 321. When attaching the junction 300 to the device main body 2, the buttons 303 are pressed, and the width between locking hooks 322 is narrowed. Then, by inserting the junction 300 into the attachment slot of the device main body 2, the female connector 305 locks in with the male connector 318 of the device main body, and the duct plug 304 locks in with the duct plug hole 319. Further, the locking hooks 322 locks into the locking holes 320 of the device main body 2. According to this mechanism, the junction 300 is securely attached to the device main body 2.

Further, it is possible to detach the junction 300 from the device main body 2 after use by pressing the buttons 303, disengaging the locking hooks 322 from the locking holes 320 of the device main body 2 and pulling away from the device main body 2.

When attaching the junction 300 to the device main body 2, since the locking hooks 322 are plate springs they have a certain degree of flexibility, and can be inserted into the attachment slot of the device main body 2 without pressing buttons 303. However, for smoother and safer attachment of the junction 300 to the device main body 2, it is better to press the buttons in order to decrease the width between the locking hooks 322.

<The Structure of the Photoplethysmographic Sphygmomanometer>

FIG. 19 is a block diagram showing the makeup of an operation circuit 100 in device main body 2 when ear-type sphygmomanometer 1 of FIG. 2 is structured as a photoplethysmographic sphygmomanometer.

Referring to FIG. 19, the interior of the inner cuff assembly 6 of the holding member 3 to be attached to the tragus incorporates the LED 20 as a light-emitting element and the phototransistor 21 as a light-receiving element forming a photoplethysmographic sensor (pulse wave sensor). The above described duct 4 is a rubber duct (air tube), and forms an air channel to the inner cuff 6. A pressurizing pump 108 has a small electric motor as a driving source, supplies pressurized air to a condenser tank 107, and supplies pressurized air into the inner cuff assembly 6 after rectification. A rapid exhaust valve 104 branched from the duct 4 has a solenoid valve mechanism (not shown), and rapidly reduces the internal pressure of the inner cuff assembly 6. A slow exhaust valve 105 that is similarly branched reduces the internal pressure of the inner cuff assembly 6 at a predetermined rate (e.g., 2 to 3 mm Hg/sec). Also, a pressure sensor 106 branched from the duct 4 changes an electrical parameter in accordance with the internal pressure of the cuff 6. A pressure detection amplifier (AMP) 107 connected to the pressure sensor 106 detects the electrical parameter of the pressure sensor 106, converts the parameter into an electrical signal, and amplifies the signal, thereby outputting an analog cuff pressure signal P.

The LED 20 irradiates a pulsing blood flow with light, and the phototransistor 21 detects the reflected light from the blood flow. A filter AMP 109 connected by the wiring 5 is a pulse wave detection amplifier, and outputs an analog pulse wave signal M by amplifying the output signal from the phototransistor 21. The wiring 5 connect the LED 20 to a light amount controller 118 that automatically changes the amount of light, and connect the pulse wave detection amplifier 109 to a gain controller 119a that automatically changes the gain, and a time constant controller 119b that changes the time constant of a filter amplifier (not shown) forming the pulse wave detection filter amplifier 109. Also, an A/D converter (A/D) 110 connected as shown in FIG. 20 converts the analog signals M and P into digital data D.

A controller (CPU) 111 performs main control of the photoplethysmographic sphygmomanometer. The CPU 111 has an adjusted pressure register 111a that stores an adjusted pressure. A ROM 112 contains a control program (to be described later) executed by the CPU 111. A RAM 113 includes a data memory, image memory, and the like. A liquid crystal display (LCD) 114 displays the contents of the image memory. An operation unit 116 is operated by the user to, for example, input a measurement start command or set an adjusted pressure value. A buzzer 115 notifies the user that, for example, the apparatus has sensed pressing of a key in the operation unit 116, or the measurement is complete. Note that the adjusted pressure register 111a is allocated in the CPU 111 in this embodiment, but an adjusted pressure storage unit may also be allocated in the RAM 113.

A dot matrix type display panel is used as the display panel 114 of the LCD, so the display panel 114 can display various kinds of information (e.g., characters, Figs., and signal waveforms). The operation panel 116 has a measurement start switch (ST) and keys for inputting, for example, a cuff pressure value. The apparatus further includes a power supply unit 121 having an exchangeable battery, and a power switch (not shown).

Furthermore, the device main body 2 has an external communication unit to be connected to a connector or cell phone (neither is shown). By connecting this external communication unit to a personal computer, it is possible to exchange various kinds of data with and save the blood pressure measurement results in an operation control parameter setting unit, data clear unit, and data saving unit of the personal computer.

FIG. 20 is a view showing the layout of the parts of the device main body 2 shown in FIG. 2, in which the lid is removed from the device main body 2. In FIG. 20, the same reference numerals as above denote the already explained arrangements or parts, and a repetitive explanation will be omitted. The device main body 2 has a length of about 120 mm, a width of about 80 mm, a thickness of 27 mm, and an overall weight of 180 g. Since the device main body 2 is thus made as compact and light as possible, it does not interfere with everyday life even when the user always carries it.

Also, the electronic parts that perform the various kinds of control described above are mounted on a substrate 140 having a packaging area that occupies the internal space. On the other hand, the pressurizing pump 108, condenser tank 107, slow exhaust valve 105, and rapid exhaust valve 104 are connected to the duct 4 that is formed integrally with these components as described above, and have the relative positional relationship as shown above, so these components can be installed together with the power supply unit 121 containing four exchangeable AAA cells. The electronic parts are thus arranged such that the limited internal space can be effectively used. In addition, a chargeable secondary battery that can be repetitively used or commercially available AAA cells that are readily obtainable can be simply exchanged by opening and closing a lid (not shown).

<Operation of Photoplethysmographic Sphygmomanometer>

The operation of the blood pressure measuring apparatus according to this embodiment as a photoplethysmographic sphygmomanometer, an ear type blood pressure measuring apparatus, will be explained below. FIGS. 21A and 21B are flowcharts for explaining the measurement process of the blood pressure measuring apparatus (photoplethysmographic sphygmomanometer). Referring to FIGS. 21A and 21B, when the user turns on the power supply by the power switch of the apparatus, an initial self-diagnosing process (not shown) is first performed to set the initial values of the apparatus. After that, the process is started when the user presses the measurement start switch.

The cuff pressure P is read in step S101, and whether the residual pressure of a cuff 6 is equal to or smaller than a prescribed value is determined in step S102. If the residual pressure exceeds the prescribed value, the LCD 114 displays "residual pressure error" in step S123. If the residual pressure is equal to or smaller than the prescribed value, the user sets a cuff pressurization value (e.g., a value larger than a maximum blood pressure value of 120 to 210 mmHg) in step S103 using the operation unit 118, and sets the light amount and gain at predetermined values in step S104.

After the pressurization value, light amount, and gain are set, the rapid exhaust valve 104 and slow exhaust valve 105 are closed in steps S105 and S106. In step S107, the pressurizing pump 3 is driven to start pressurization (raising the pressure). This is the start of a measurement process upon pressurization, and the cuff pressure starts increasing at a constant rate (e.g., 2 to 3 mmHg/sec). In step S108, the individual functional blocks perform data processing, and measure the minimum blood pressure and maximum blood pressure. When the maximum blood pressure is measured (S109), the driving of the pressurizing pump 108 is stopped in step S112.

In step S110, it is determined whether the cuff pressure is higher than a pressurization value U set in step S103. If P<U, the cuff pressure still falls within a normal measurement range, so the measurement continues. If P>U, the cuff pressure is higher than the set value, so the LCD 114 displays "measurement error" in step S111. If necessary, the LCD 114 additionally displays detailed information such as "signal abnormality upon pressurization". In step S113, it is determined whether the signal level of a pulse wave signal obtained upon pressurization falls within a predetermined range over which highly accurate blood pressure measurement is possible. If the signal level falls within the predetermined range, the LCD 114 displays the measured maximum blood pressure value and minimum blood pressure value in step S120, and a tone signal is supplied to the buzzer 115 in step S121.

If the signal level falls outside the predetermined range in step S113, the light amount and gain are adjusted based on the signal level of the pulse wave signal in step S114. In step S114, the apparatus performs, for example, the following processing. If the carrier wave of the pulse wave is equal to or smaller than a standard value (20% to 40% of the full scale of the A/D converter 110), whether the step light amount is a maximum is checked. If the step light amount is not a maximum, the light amount is increased by controlling the light amount controller 118. If the light amount is a maximum, the gain is raised. On the other hand, if the carrier wave level is equal to or larger than the standard value, whether the gain is a minimum is checked. If the gain is not a minimum, the gain controller 119a lowers the gain by feedback control. If the gain is a minimum, the light amount is decreased.

When the adjustment of the light amount and gain is complete, the slow exhaust valve 105 is opened in step S115. This is the start of a measurement process upon depressurization (pressure withdrawal), and the cuff pressure starts reducing at a constant rate (e.g., 2 to 3 mmHg/sec). In step S116, the individual functional blocks perform data processing, and measure the maximum blood pressure (systolic blood pressure) and minimum blood pressure (diastolic blood pressure). In step S117, whether the minimum blood pressure value is detected upon depressurization is determined. If no value is detected, the measurement continues. In step S118, whether the cuff pressure is lower than a predetermined value L (e.g., 40 mmHg) is determined. If P≧L, the cuff pressure still falls within the normal measurement range, so the process returns to step S116. If P<L, the cuff pressure is lower than the normal measurement range, so the LCD 114 displays "measurement error" in step S119. If necessary, the LCD 114 additionally displays detailed information such as "signal abnormality upon depressurization".

If it is determined in step S117 that the measurement is complete, this means that the measurement process is complete within the normal measurement range. Accordingly, the LCD 14 displays the measured maximum blood pressure value and minimum blood pressure value in step S120, and a tone signal is supplied to the buzzer 115 in step S121. Preferably, different tone signals are supplied for normal termination and abnormal termination. In step S122, the remaining air in the cuff 6 is rapidly exhausted, and the start of the next measurement is awaited.

<Blood Pressure Calculations>

FIG. 22 is a graph showing the correlation between the cuff pressure and pulse wave signal. FIG. 22 shows waveforms during a time period from the start of the measurement upon pressurization (step S108) to the end of the measurement upon depressurization (step S116).

Referring to FIG. 22, blood pressure measurements are generally performed as follows. That is, in the measurement upon pressurization, the cuff pressure at point (a) at which the pulse wave signal starts changing its magnitude is the minimum blood pressure, and the cuff pressure at point (b) at which the pulse wave signal disappears is the maximum blood pressure. On the other hand, the blood pressure measurement upon depressurization is opposite to that upon pressurization; the cuff pressure at point (c) at which the pulse wave signal appears is the maximum blood pressure, and the cuff pressure at point (d) at which the pulse wave signal stops changing its magnitude is the minimum blood pressure.

Note that this embodiment has disclosed an example in which the reflected light from the blood in the blood vessel is detected, but it is also possible to detect transmitted light instead.

As explained above, the photoplethysmographic sphygmomanometer of this embodiment makes it possible to provide a photoplethysmographic sphygmomanometer capable of highly accurate measurement by adjusting the signal level of a pulse wave signal such that the signal level falls within a predetermined standard range, and also capable of reducing the physical burden on the user caused by the cuff pressure by shortening the blood pressure measurement time. Note that the tragus and its periphery are less sensitive to pain, so it is also possible to effectively reduce the pain caused by the cuff pressure. This further achieves the effect of facilitating the application of the apparatus to continuous blood pressure measurement.

Note that the above blood pressure measuring apparatus detects the pulse wave by using the light-emitting element 20 and light-receiving element 21, but it is also possible to detect the pulse wave by sensing the pulsation (oscillation) of the blood vessel on the surface of a living body as a pressure change by using a cuff that applies pressure to the tragus. That is, a cuff to which pressure is applied converts the pulsation obtained from a living body into a pressure change in the cuff, and a pressure sensor senses this pressure change in the cuff. This arrangement can also detect the pulse wave of a living body. It is also possible to install a miniature microphone in a cuff portion in contact with a living body, detect Korotkoff sounds generated when the cuff presses a portion of the living body, and measure the blood pressure based on the generation or disappearance of Korotkoff sounds equal to or higher than a predetermined level.

OTHER EMBODIMENTS

In the above embodiment, only one (the interior of the inner cuff assembly 6) of the pair of cuffs having the arrangement that clamps the tragus 221 has the irradiating portion (LED 20) that irradiates the blood-flow in the blood vessel with light, and the light-receiving portion (phototransistor 21) that detects the reflected light from the blood flow. However, it is also possible to set up a so called "reflective type" by installing the LED 20 and the phototransistor 21 in both the inner and outer cuffs 6 and 7, which allows simultaneous measurements of blood pressure from both faces of the tragus. Further, instead of using the photoplethysmographic method, pressure pulse method can be implemented which eliminates the need to install an LED and a phototransistor within the cuffs. This in turn can simplify the device by further eliminating the wiring and a light amount controller needed only for the photoplethysmographic type.

As described above, it is also possible to arrange sensors in both the inner and outer cuffs, and simultaneously measure the blood pressures on the back side and front side of the tragus. In this arrangement, one cuff can press the blood vessel (arteriole) on the back side of the external ear and its periphery, and the other cuff can press the superficial temporal artery or its branched blood vessel on the front side of the external ear and its periphery. Note that the blood pressure in the external ear and its periphery (more specifically, the tragus and its periphery) is measured for the following reason as well.

That is, the blood vessel (arteriole) in the tragus and its periphery is close to the blood vessels in the brain, so it is presumably possible to measure the change in blood pressure resulting from the brain. As well, in the tragus and its periphery, the artery (superficial temporal artery) that directly connects to the heart exists in addition to the blood vessel (arteriole) existing in the cartilage (primarily the tragus) of the ear. In the tragus and its periphery, therefore, a small apparatus can simultaneously measure the blood pressures having different kinds of information (i.e., the blood pressure resulting from the brain and the blood pressure resulting from the heart). The photoplethysmographic sphygmomanometer of this embodiment can set the signal level of the pulse wave signal within the predetermined standard range, and can accurately measure the blood pressure in the external ear and its periphery. At the same time, it is possible to shorten the blood pressure measurement time, thereby reducing the physical burden on the user caused by the cuff pressure.

As stated above, it is possible to accurately measure the blood pressure with the photoplethysmographic sphygmomanometer of this embodiment by setting the signal level of the pulse wave signal within the predetermined standard range, and also the physical burden on the user caused by the cuff pressure by shortening the blood pressure measurement time.

Additionally, said blood pressure measuring device detects pulse waves using the LED 20 and the phototransistor 21, but it is also possible to detect pulse waves with cuffs that apply pressure to the region where measurement is being made and capture pulse waves as changes in pressure.

In other words, pulsation detected from a living body is converted to changes in pressure that occurs within the cuffs, and detects this pressure changes using a pressure detecting device. It is also possible to detect pulsation of a living body using such methods. Further, it is acceptable to install a compact microphone in a cuff portion in contact with a living body, detect Korotkoff sounds generated when the cuff presses a portion of the living body, and measure the blood pressure based on the generation or disappearance of Korotkoff sounds equal to or higher than a predetermined level.

The present invention is not limited to the above embodiments, and various changes and modifications can be made without departing from the spirit and scope of the invention. Therefore, to apprise the public of the scope of the present invention, the following claims are made.

The invention claimed is:

1. Blood pressure measuring cuffs which measures blood pressure using an inner cuff which is adapted to be inserted into the acoustic canal and an outer cuff which is adapted to be placed on the outer surface of the tragus,
   wherein said inner cuff and outer cuff are comprised of:
      a cuff member connected to a duct, and a cuff bladder fixed onto said cuff member in an air-tight manner and has a body which can expand and contract, wherein a lid of said cuff bladder has a pressing surface formed in a shape of either a protrusion or a collapsed protrusion, and wherein said lid is circular, the diameter of said cuff bladder is within a range of 5 to 10 mm, the diameter of said pressing surface is within a range of 3 to 6 mm, the thickness of said pressing surface is within a range of 0.4 to 1 mm, and the thickness of said body is within a range of 0.1 to 0.8 mm.

2. Blood pressure measuring cuffs according to claim 1 characterized in that, said cuff bladder is integrally molded from an elastic material including silicon rubber, natural rubber, and predetermined synthetic resin materials having a Shore hardness value of 30 to 60.

3. Blood pressure measuring cuffs according to claim 1 characterized in that, an optical means comprised of a light-emitting element and a light receiving element is installed inside said cuff(s) which capture signals from absorption and reflection of light caused by blood flowing through blood vessels, and a hole is drilled on said pressing surface after forming said cuff bladder from a light shielding material, and into said hole a light permeable layer is inserted and is integrally formed by vulcanization as a single piece light shielding layer, excluding the designated area of said pressing surface of said inner cuff inserted with the light permeable layer.

4. Blood pressure measuring cuffs according to claim 1 characterized in that, a hole is drilled on said pressing surface after forming said cuff bladder from a light shielding material, and into said hole a light permeable layer is inserted and is integrally formed by vulcanization as a single piece light shielding layer, excluding the designated area of said pressing surface of said inner cuff inserted with the light permeable layer, and at the same time, said light permeable layer has a shape of a circle, an ellipse or an oval, and is formed concentrically or with its center offset.

5. Blood pressure measuring cuffs which measures blood pressure using an inner cuff which is adapted to be inserted in to the acoustic canal and an outer cuff which is adapted to be placed on the outer surface of the tragus, wherein said inner cuff and outer cuff are comprised of:
a cuff member connected to a duct, and
a cuff bladder fixed onto said cuff member in an air-tight manner and has a body which can expand and contract, and wherein a lid of said cuff bladder has a pressing surface formed in a shape of either a protrusion or a collapsed protrusion, and wherein said lid is elliptical or oval, the major axis is within a range of 5 to 15 mm, the minor axis is within a range of 4 to 10 mm, the thickness of said pressing surface is within a range of 0.4 to 1 mm, and the thickness of said body is within a range of 0.1 to 0.8 mm.

6. A blood pressure measuring device, comprising:
an inner cuff to be inserted into the acoustic canal and an outer cuff to be placed on the outer surface of the tragus;
a holding means for holding said inner cuff and said outer cuff;
a pulse wave detection means installed in at least one of said inner cuff and said outer cuff, for detecting pulse wave signals from blood flowing through blood vessels;
a pressure adjusting means, for applying and decreasing pressure using a fluid body including air to said inner cuff and outer cuff that are adapted to pinch the tragus;
ducts for supplying a fluid body connecting said inner cuff and said outer cuff to said pressure adjusting means;
a pressure detecting means for detecting pressures of said inner cuff and said outer cuff;
a blood pressure measurement controlling means for measuring blood pressure from said pulse wave signals, and
wiring which connects said pulse wave detection means and said blood pressure measurement controlling means,
wherein said inner cuff and outer cuff are comprised of:
a cuff member connected with said ducts, and
a cuff bladder fixed onto said cuff member in an air-tight manner and has a lid and a body which can expand and shrink, and forms a pressing surface configured as a protrusion on the lid of said cuff bladder, and
wherein the lid of said cuff bladder is circular, the diameter of said cuff bladder is within a range of 5 to 10 mm, the diameter of said pressing surface is within a range of 3 to 6 mm, the thickness of said pressing surface is within a range of 0.4 to 1 mm, and the thickness of said body is within a range of 0.1 to 0.8 mm.

7. A blood pressure measuring device, comprising:
an inner cuff to be inserted into the acoustic canal and an outer cuff to be placed on the outer surface of the tragus;
a holding means for holding said inner cuff and said outer cuff;
a pulse wave detection means installed in at least one of said inner cuff and said outer cuff, for detecting pulse wave signals from blood flowing through blood vessels;
a pressure adjusting means, for applying and decreasing pressure using a fluid body including air to said inner cuff and outer cuff that are adapted to pinch the tragus;
ducts for supplying a fluid body connecting said inner cuff and said outer cuff to said pressure adjusting means;
a pressure detecting means for detecting pressures of said inner cuff and said outer cuff;
a blood pressure measurement controlling means for measuring blood pressure from said pulse wave signals, and
wiring which connects said pulse wave detection means and said blood pressure measurement controlling means,
wherein said inner cuff and outer cuff are comprised of:
a cuff member connected with said ducts, and
a cuff bladder fixed onto said cuff member in an air-tight manner and has a lid and a body which can expand and shrink, and forms a pressing surface configured as a protrusion on the lid of said cuff bladder, and
wherein the lid of said cuff bladder is elliptical or oval, the major axis is within a range of 5 to 15 mm, the minor axis is within a range of 4 to 10 mm, the thickness of said pressing surface is within a range of 0.4 to 1 mm, and the thickness of said body is within a range of 0.1 to 0.8 mm.

* * * * *